US005614366A

United States Patent [19]

Reyes et al.

[11] Patent Number: 5,614,366

[45] Date of Patent: Mar. 25, 1997

[54] HTLV-I PEPTIDE ANTIGENS AND KIT

[75] Inventors: Gregory R. Reyes, Palo Alto; Kenneth G. Hadlock, Hayward, both of Calif.

[73] Assignee: Genelabs Technologies, Inc., Redwood City, Calif.

[21] Appl. No.: 653,091

[22] Filed: Feb. 8, 1991

Related U.S. Application Data

[63] Continuation-in-part of Ser. No. 366,313, Jun. 13, 1989, Pat. No. 5,066,579, which is a continuation of Ser. No. 948,270, Dec. 31, 1986, abandoned.

[51] Int. Cl.[6] .......... G01N 33/53; C12Q 1/70; C07K 5/00; C07K 7/00

[52] U.S. Cl. .......... 435/7.1; 435/5; 530/324

[58] Field of Search .......... 530/324; 435/7.1, 435/5

[56] References Cited

U.S. PATENT DOCUMENTS

| | | | |
|---|---|---|---|
| 4,446,122 | 5/1984 | Chu et al. . | |
| 4,525,300 | 6/1985 | Yoshida et al. . | |
| 4,572,800 | 2/1986 | Shimizu et al. . | |
| 4,588,681 | 5/1986 | Sawada et al. . | |
| 4,645,738 | 2/1987 | Knowles et al. . | |
| 4,661,445 | 4/1987 | Saxinger et al. . | |
| 4,663,436 | 5/1987 | Elder et al. . | |
| 4,689,398 | 8/1987 | Wu et al. . | |
| 4,722,888 | 2/1988 | Broder et al. . | |
| 4,724,258 | 2/1988 | Yoshida et al. . | |
| 4,731,326 | 3/1988 | Thompson et al. . | |
| 4,735,896 | 4/1988 | Wang et al. . | |
| 4,743,678 | 5/1988 | Essex et al. . | |
| 4,757,000 | 7/1988 | Tohmatsu et al. . | |
| 5,003,043 | 3/1991 | Akita et al. | 530/324 |
| 5,017,687 | 5/1991 | Vahlne et al. | 530/324 |
| 5,039,604 | 8/1991 | Papsidero . | |
| 5,066,579 | 11/1991 | Reyes | 435/5 |

FOREIGN PATENT DOCUMENTS

| | | |
|---|---|---|
| 0166224 | 5/1985 | European Pat. Off. . |
| 0214555 | 8/1986 | European Pat. Off. . |
| 0246101 | 5/1987 | European Pat. Off. . |
| 0267622 | 11/1987 | European Pat. Off. . |
| 0269445 | 11/1987 | European Pat. Off. . |
| 2122343 | 4/1983 | United Kingdom . |
| 86/01834 | 3/1986 | WIPO . |

OTHER PUBLICATIONS

Ralston, et al, 1989, "Identification and Synthesis of the Epitope . . . " J. Biol. Chem. 264(28):16343–16346.
Kowalski, et al, 1987, "Functional Regions of the envelope . . . " Science 237:1351–1355.
Huynh et al., in *DNA Cloning, vol. 1* (ed. D.M. Glover, Washington, D.C.:IRL Press, 1985), pp. 49–78.
Miyoshi et al., Nature 294:770–771 (1981).
Popovic et al., Science 219:856–859 (1983).
Anderson, D. W. et al., Blood 74,7:2585–2591 (1989).
Blattner, W. A. et al., Int. J. Cancer 30:257–264 (1982).
Blattner, W. A. et al., JAMA 250,8:1074–1080 (1983).
Blayney, D. W. et al., JAMA 250,8:1048–1052 (1983).
Catovsky, D. et al., Lancet, 04/20/82:639–643 (1982).
Chen, Y–M. A. et al., J. Virology 63,11:4952–4957 (1989).
Chen, Y–M. A. et al., Lancet 336:1153–1155 (1990).
Chiba, J. et al., Proc. Natl. Acad. Sci. USA 88:4641–4645 (1991).
Cianciolo, G. J. et al., Science 230:453–455 (1985).
Clapham, P. et al., Proc. Natl. Acad. Sci. USA 81:2886–2889 (1984).
Essex, M. et al., Science (Sep.):1061–1064 (1983).
Gallo, R. C. et al., Proc. Natl. Acad. Sci. USA 79:5680–5683 (1982).
Gallo, R. C. et al., Cancer Res. 43:3892–3899 (1983).
Halbert, S. P. et al., J. Clin. Microbiol. 23,2:212–216 (1986).
Hattori, S. et al., Virology 136:338–347 (1984).
Itamura, S. et al., Gene 38:57–64 (1985).
Iwatsuki, K. et al., Jpn. J. Dermatol. 99:1059–1065 (1989).
Kiyokawa, T. et al., Proc. Natl. Acad. Sci. USA 81:6202–6206 (1984).
Kline, R. L. et al., Lancet 337:30–33 (1991).
Lal, R. B. et al., J. Infect. Dis. 163:41–46 (1991).
Lee, T. H. et al., Proc. Natl. Acad. Sci. USA 81:3856–3860 (1984).
Lillehoj, E. P. et al., J. Clin. Microbiol. 28, 12:2653–2658. (1990).
Matsushita, S. et al., Proc. Natl. Acad. Sci. USA 83:2672–2676 (1986).
Newman, M. J. et al., Virology 150:106–116 (1986).
Nyunoya, H. et al., AIDS Res. H. Retrovirus 6, 11:1311–1321 (1990).
Oroszlan, S. and Copeland, T. D., Current Topics in Microbiol. and Immunol. 115:221–233 (1985).
Palker, T. J. et al., J. Immunol. 142:971–978 (1989).
Patarca, R. and Haseltine, W. A., Nature 309:728 (1984).
Poiesz, B. J. et al., Proc. Natl. Acad. Sci. USA 77:7415–7419 (1980).
Poiesz, B. J. et al., Nature 294:268–271 (1981).
Ralph, R. K., Nature 311:515 (1984).
Robert–Guroff, M. et al., J. Exper. Med. 154:1957–1964 (1981).
Robert–Guroff, M. et al., J. Exper. Med. 157:248–258 (1983).
Robert–Guroff, M. and Shepard, E., J. Virology 53, 1:214–220 (1985).
Samuel, K. P. et al., Science 236:1094–1097 (1984).
Saxinger, W. et al., Science (Sep. 28):1473–1476 (1984).
Schupbach, J. et al., Science 224:607–610 (1984).

(List continued on next page.)

*Primary Examiner*—Lynette R. F. Smith
*Attorney, Agent, or Firm*—Allan A. Brookes; Gary R. Fabian; Peter J. Dehlinger

[57] ABSTRACT

Novel HTLV-I and HTLV-II peptide antigens are disclosed for use in diagnostics assays for screening and confirming HTLV-I and HTLV-II antisera. The peptides are derived from analogous regions of HTLV-I and HTLV-II gp46 envelope proteins, and are differentiated by their immunoreactivity with an HTLV-II specific monoclonal antibody and by HTLV-I and HTLV-II antisera. The peptides are also useful in vaccine compositions.

2 Claims, 8 Drawing Sheets

OTHER PUBLICATIONS

Seiki, M. et al., Proc. Natl. Acad. Sci. USA 80:3618–2622 (1983).
Shimoyama, M. et al., Jpn. J. Clin. Oncol. 12,1:109–116 (1982).
Slamon, D. J. et al., Report 5 Oct.:291–299 (1984).
Sodroski, J. et al., Report 27 Jul.:241–245 (1984).
Sugamura, K. et al., J. Immun. 132,6:3180–3184 (1984).
Tanaka, Y. et al., Int. J. Cancer 36:549–555 (1985).
Tanaka, Y. et al., Int. J. Cancer 46:675–681 (1990).
Wang, J. J. G. et al., Proc. Natl. Acad. Sci. USA 83:6159–6163 (1986).
Williams, A. E. et al., Science 240:643–646 (1988).
Williams, A. E. et al., MMWR 39,50:915–924 (1990).
Yoshida, M. et al., Proc. Natl. Acad. Sci. USA 79:2031–2035 (1982).

ThrGlyAlaValSerSerProTyrTrpLysPheGlnHisAspValAsnPheThrGlnGluValSerArgLeuAsnIle
TACAGGAGCCGTCTCCAGCCCCTACTGGAAGTTTCAGCACGATGTCAATTTTACTCAAGAAGTTTCACGCCTCAATATT
5565

AsnLeuHisPheSerLysCysGlyPheProPheSerLeuLeuValAspAlaProGlyTyrAspProIleTrp
AATCTCCATTTTTCGAAATGCGGTTTTCCCTTCTCCCTTCTAGTCGACGCTCCAGGATATGACCCCATCTG 5700
5664

PheLeuAsnThrGluProSerGlnLeuProProThrAlaProProLeuLeuProHisSerAsnLeuAspHisIleLeu
GTTCCTTAATACCGAACCCAGCCAACTGCCTCCCACCGCCCCTCCTCTACTCCCCCACTCTAACCTAGACCACATCCTC

GluProSerIleProTrpLysSerLysLeuLeuThrLeuValGlnLeuThrLeuGlnSerThrAsnTyrThr
GAGCCCTCTATACCATGGAAATCAAAACTCCTGACCCTTGTCCAGTTAACCCTACAAAGCACTAATTATACT 5850
5790 5807

CysIleValCysIleAspArgAlaSerLeuSerThrTrpHisValLeuTyrSerProAsnValSerValProSerSer
TGCATTGTCTGTATCGATCGTGCCAGCCTATCCACTTGGCACGTCCTATACTCTCCCAACGTCTCTGTTCCATCCTCT
5895

SerSerThrProLeuLeuTyrProSerLeuAlaLeuProAlaProHisLeuThrLeuProPheAsnTrpThr
TCTTCTACCCCCCTCCTTTACCCATCGTTAGCGCTTCCAGCCCCCCACCTGACGTTACCATTTAACTGGAC

Fig. 2

```
                                   HILEPSIPWKSKLLTLVQL                                      K164
                               HSNLDHILEPS                                                  K162
                          TAPPLLPHSNLDHILEPS                                                K163

 gt-SLLVDAPGYDPIWFLNTEPSQLPPTAPPLLPHSNLDHILEPSIPWKSKLLTLVQLTLQSTJYYCIVCIDRASLSTHV-gt       MTA-5
 gt-SLLVDAPGYDPIWFLNTEPSQLPPTAPPLLPHSNLDHILEPSIPWKSK-gt                                    MTA-1
CGFPSSLLVDAPGYDPIWFLNTEPSQLPPTAPPLLPHSNLDHILEPS-gt                                         MTA-4

CGFPFSLLVDAPGYDPIWFLNTEPSQLPPTAPPLLPHSNLDHILEPSIPWKSKLLTLVQLTLQSTNYYCIVCIDRASLSTWHVLY-   HLTV-1
||    ||||||||||| ||   || ||| |||  | | | | ||| | |  |  ||||||||| || || ||| |||||
CGSSMTLLVDAPGYDPLWFITSEPTQPPPTSPPLVHDSDLEHVLTPSTSWTTKILKFIQLTLQSTNYSCMVCVDRSSLSSWHVLY-   HTLV-1I

gt-MTLLVDAPGYDPLWFITSEPTQPPPTSPPLVHDSDLEHVLTPSTSWTTK-gt                                   GH2-K15
   MTLLVDAPGYDPLWFITSEPTQPPPTSPPLVHDSDLEHVLTPS                                              K14
   MTLLVDAPGYDPLWFITSEPTQPPPTS                                                              K16
            WFITSEPTQPPPTSPPLVHDSDLEHVLTPS                                                  K24
                         SPPLVHDSDLEHVLTPSTSWTTK                                            K35
                         SPPLVHDSDLEHVLTPS                                                  K34

                                 EHVLTPSTSWTT                                               K169
                         SPPLVHDSDLEHVLTPSTSWTT                                             K170
                         SPPLVHDSDLEHVLTPS                                                  K125
            WFITSEPTQPPPTS                                                                  K126
   MTLLVDAPGYDPLW                                                                           K128
```

Fig. 3

```
5521      5531      5541      5551      5561      5571
TGGACATCCGCATACACGGGCCCCGTCTCCAGTCCATCCTGGAAGTTTCATTCAGA

5581      5591      5601      5611      5621      5631
TGTAAATTTCACCCAGGAAGTCAGCCAAGTGTCCCTTCGACTACACTTCTCTAAGTGCGG

          M  T  L  L  V  D  A  P  G  Y  D  P  L  W  F  I  T  S
5641      5651      5661      5671      5681      5691
CTCCTCCATGACCCTCCTAGTAGATGCCCCTGGATATGATCCTTTATGGTTCATCACCTC
(KAE1=)ATGACCCTCCTAGTAGATGCC-->

 E  P  T  Q  P  P  P  T  S  P  P  L  V  H  D  S  D  L  E  H
5701      5711      5721      5731      5741      5751
AGAACCCACTCAGCCTCCACCAACTTCTCCCCCATTGGTCCATGACTCCGACCTTGAACA

 V  L  T  P  S  T  S  W  T  T  K
 5761      5771      5781      5791      5801      5811
TGTCCTAACCCCCTCCACGTCCTGGACGACCAAAATACTCAAATTTATCCAGCTGACCTT
          <--AGGTGCGGACCACGTGGTTTT     =(KAE5)
CAG^CTG(PvuII)

5821      5831      5841      5851      5861      5871
ACAGAGCACCAATTACTCCTGCATGGTTTGCGTGGATAGATCCAGCCTCTCATCCTGGCA

5881      5891      5901      5911      5921      5931
TGTACTCTACACCCCCAACATCTCCATTCCCCAACAAACCTCCTCCCGAACCATCCTCT
```

Fig. 6

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 47 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-I ( x i ) SEQUENCE DESCRIPTION: SEQ ID NO:1:

```
Leu Leu Val Asp Ala Pro Gly Tyr Asp Pro Ile Trp Phe Leu Asn Thr
1               5                   10                  15

Glu Pro Ser Gln Leu Pro Pro Thr Ala Pro Pro Leu Leu Pro His Ser
            20                  25                  30

Asn Leu Asp His Ile Leu Glu Pro Ser Ile Pro Trp Lys Ser Lys
        35                  40                  45
```

( 2 ) INFORMATION FOR SEQ ID NO:2:

( i ) SEQUENCE CHARACTERISTICS:
( A ) LENGTH: 41 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-I ( x i ) SEQUENCE DESCRIPTION: SEQ ID NO:2:

```
Leu Leu Val Asp Ala Pro Gly Tyr Asp Pro Ile Trp Phe Leu Asn Thr
1               5                   10                  15

Glu Pro Ser Gln Leu Pro Pro Thr Ala Pro Pro Leu Leu Pro His Ser
            20                  25                  30

Asn Leu Asp His Ile Leu Glu Pro Ser
        35                  40
```

( 2 ) INFORMATION FOR SEQ ID NO:3:

( i ) SEQUENCE CHARACTERISTICS:
( A ) LENGTH: 6 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-I ( x i ) SEQUENCE DESCRIPTION: SEQ ID NO:3:

```
Ile Pro Trp Lys Ser Lys
1               5
```

( 2 ) INFORMATION FOR SEQ ID NO:4:

( i ) SEQUENCE CHARACTERISTICS:
( A ) LENGTH: 18 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-I ( x i ) SEQUENCE DESCRIPTION: SEQ ID NO:4:

```
Thr Ala Pro Pro Leu Leu Pro His Ser Asn Leu Asp His Ile Leu Glu
1               5                   10                  15

Pro Ser
```

( 2 ) INFORMATION FOR SEQ ID NO:5:

( i ) SEQUENCE CHARACTERISTICS:
( A ) LENGTH: 49 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-II ( x i ) SEQUENCE DESCRIPTION: SEQ ID NO:5:

```
Met Thr Leu Leu Val Asp Ala Pro Gly Tyr Asp Pro Leu Trp Phe Ile
1               5                   10                  15

Thr Ser Glu Pro Thr Gln Pro Pro Pro Thr Ser Pro Pro Leu Val His
            20                  25                  30

Asp Ser Asp Leu Glu His Val Leu Thr Pro Ser Thr Ser Trp Thr Thr
        35                  40                  45

Lys
```

( 2 ) INFORMATION FOR SEQ ID NO:6:

( i ) SEQUENCE CHARACTERISTICS:
( A ) LENGTH: 23 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-II ( x i ) SEQUENCE DESCRIPTION: SEQ ID NO:6:

Ser Pro Pro Leu Val His Asp Ser Asp Leu Glu His Val Leu Thr Pro
1 5 10 15

Ser Thr Ser Trp Thr Thr Lys
20

( 2 ) INFORMATION FOR SEQ ID NO:7:

( i ) SEQUENCE CHARACTERISTICS:
( A ) LENGTH: 17 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-II ( x i ) SEQUENCE DESCRIPTION: SEQ ID NO:7:

Ser Pro Pro Leu Val His Asp Ser Asp Leu Glu His Val Leu Thr Pro
1 5 10 15

Ser ( 2 ) INFORMATION FOR SEQ ID NO:8:

( i ) SEQUENCE CHARACTERISTICS:
( A ) LENGTH: 6 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-II ( x i ) SEQUENCE DESCRIPTION: SEQ ID NO:8:

Thr Ser Trp Tyr Tyr Lys
1 5

( 2 ) INFORMATION FOR SEQ ID NO:9:

( i ) SEQUENCE CHARACTERISTICS:
( A ) LENGTH: 13 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-I ( x i ) SEQUENCE DESCRIPTION: SEQ ID NO:9:

Leu Pro His Ser Asn Leu Asp His Ile Leu Glu Pro Ser
1 5 10

( 2 ) INFORMATION FOR SEQ ID NO:10:

( i ) SEQUENCE CHARACTERISTICS:
( A ) LENGTH: 6 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: HTLV-I ( x i ) SEQUENCE DESCRIPTION: SEQ ID NO:10:

His Ile Leu Glu Pro Ser
1 5

( 2 ) INFORMATION FOR SEQ ID NO:11:

( i ) SEQUENCE CHARACTERISTICS:
( A ) LENGTH: 2549 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: HTLV-I ( x i ) SEQUENCE DESCRIPTION: SEQ ID NO:11:

ACAGGAGCCG TCTCCAGCCC CTACTGGAAA TTTCAGCAAG ATGTCAATTT TACTCAAGAA 60

GTTTCACACC TCAATATTAA TCTCCATTTT TCAAAATGCG GTTTTTCCTT CTCCCTTCTA 120

GTCGACGCTC CAGGATATGA CCCCATCTGG TTCCTTAATA CCGAACCCAG CCAACTGCCT 180

CCCACCGCCC CTCCTCTACT CTCCCACTCT AACCTAGACC ATATCCTCGA GCCCTCTATA 240

CCATGGAAAT CAAAACTCCT GACTCTTGTC CAGTTAACCC TACAAAGCAC TAATTATACT 300

TGCATTGTCT GTATCGATCG TGCCAGCCTA TCCACTTGGC ACGTCCTATA CTCTCCCAAC 360

GTCTCTGTTC CATCCCCTTC TTCTACCCCC CTCCTTTACC CATCGTTAGC GCTTCCAGCC 420

CCCCACCTGA CGTTACCATT TAACTGGACT ATGCTGCCCA GAACAGACGA GGCCTTGATC 480

-continued

```
TCCTGTTCTG GGAGCAAGGA GGATTATGCA AAGCATTACA AGAACAGTGC TGTTTTCTAA  540
ATATTACTAA TTCCCATGTC TCAATACTAC AAGAGAGACC CCCCCTTGAA AATCGAGTCC  600
TGACTGGCTG GGGCCTTAAC TGGGACCTTG GCCTCTCACA GTGGGCTCGA GAAGCCTTAC  660
AAACTGGAAT CACCCTTGTC GCGCTACTCC TTCTTGTTAT CCTTGCAGGA CCATGCATCC  720
TCCGTCAGCT ACGACACCTC CCCTCGCGCG TCAGATACCC CCATTACTCT CTTATAAACC  780
CTGAGTCATC CCTGTAAACC AAGCACACAA TTATTGCAAC CACATCGCCT CCAGCCTCCC  840
CTGCCAATAA TTAACCTCTC CCATCAAATC CTCCTTCTCC TGCAGCAACC TCCTCCGTTC  900
AGCCTCCAAG GACTCCACCT CGCCTTCCAA CTGTCTAGTA TAGCCATCAA CCCCCAACTC  960
CTGCATTTTT TCTTTCCTAG CACTATGCTG TTTCGCCTTC TCAGCCCCTT GTCTCCACTT 1020
GCGCTCACGG CGCTCCTGCT CTTCCTGCTT TCTCCGGGCG AAGTCAGCGG CCTTCTCCTC 1080
CGCCCGCTTC CTGCGCCGTG CCTTCTCCTC TTCCTTCCTT TTCAAATACT CAGCAATCTG 1140
CTTTTCCTCC TCTTTCTCCC GCTCTTTTTT TCGCTTCCTC TTCTCCTCAG CCCGTCGCTG 1200
CCGATCACGA TGCGTTTCCC CGCGAGGTGG CGCTTTCCCC CCTGGAGGGC CCCGTCGCAG 1260
CCGGCCGCGG CTTTCCTCTT CTAGAGATAG CAAACCGTCA AGCACAGTTT CCTCCTCCTC 1320
CTTGTCCTTT AACTCTTCCT CCAAGGATAA TAGCCCGTCC ACCAATTCCT CCACCAGCAG 1380
GTCCTCCGGG CATGGAACAG GCAAACATCG AAACAGCCCT ACGGATACAA AGTTAACCAT 1440
GCTTATTATC AGCCCACTTC CCAGGGTTTG GACAGAGTCT TCTTTTCGGA TACCCAGTCT 1500
ACGTGTTTGG AGACTGTGTA CAAGGCGACT GGTGCCCCAT CTCTGGGGGA CTATGTTCGG 1560
CCCGCCTACA TCGTCACGCC CTACTGGCCA CCTGTCCAGA GCATCAGATC ACCTGGGACC 1620
CCATCGATGG ACGCGTTATC GGCTCAGCTC TACAGTTCCT TATCCCTCGA CTCCCCTCCT 1680
TCCCCACCCA GAGAACCTCT AAGACCCTTA AGGTCCTTAC CCCGCCAATC ACTCATACAA 1740
CCCCCAACAT TCCACCCTCC TTCCTCCAGG CCATGCGCAA ATACTCCCCC TTCCGAAATG 1800
GATACATGGA ACCCACCCTT GGGCAGCACC TCCCAACCCT GTCTTTTCCA GACCCCGGAC 1860
TCCGGCCCCA AAACCTGTAC ACCCTCTGGG GAGGCTCCGT TGTCTGCATG TACCTCTACC 1920
AGCTTTCCCC CCCCATCACC TGGCCCCTCC TGCCCCATGT GATTTTTTGC CACCCCGGCC 1980
AGCTCGGGGC CTTCCTCACC AATGTTCCCT ACAAACGAAT AGAAAAACTC CTCTATAAAA 2040
TTTCCCTTAC CACAGGGGCC CTAATAATTC TACCCGAGGA CTGTTTGCCC ACCACCCTTT 2100
TCCAGCCTGC TAGGGCACCC GTCACGCTGA CAGCCTGGCA AAACGGCCTC CTTCCGTTCC 2160
ACTCAACCCT CACCACTCCA GGCCTTATTT GGACATTTAC CGATGGCACG CCTATGATTT 2220
CCGGGCCCTG CCCTAAAGAT GGCCAGCCAT CTTTAGTACT ACAGTCCTCC TCCTTTATAT 2280
TTCACAAATT TCAAACCAAG GCCTACCACC CCTCATTTCT ACTCTCACAC GGCCTCATAC 2340
AGTACTCTTC CTTTCATAAT TTGCATCTCC TATTTGAAGA ATACACCAAC ATCCCCATTT 2400
CTCTACTTTT TAACGAAAAA GAGGCAGATG ACAATGACCA TGAGCCCCAA ATATCCCCCG 2460
GGGGCTTAGA GCCTCTCAGT GAAAAACATT TCCGTGAAAC AGAAGTCTGA GAAGGTCAGG 2520
GCCCAGAATA AGGCTCTGAC GTCTCCCCC                                  2549
```

( 2 ) INFORMATION FOR SEQ ID NO:12:

( i ) SEQUENCE CHARACTERISTICS:

( A ) LENGTH: 416 base pairs ( B ) TYPE: nucleic acid ( C ) STRANDEDNESS: double ( D ) TOPOLOGY: linear -continued ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: HTLV-II ( x i ) SEQUENCE DESCRIPTION: SEQ ID NO:12:

```
TGGACATCCG CATACACGGG CCCCGTCTCC AGTCCATCCT GGAAGTTTCA TTCAGATGTA    60
AATTTCACCC AGGAAGTCAG CCAAGTGTCC CTTCGACTAC ACTTCTCTAA GTGCGGCTCC   120
TCCATGACCC TCCTAGTAGA TGCCCCTGGA TATGATCCTT TATGGTTCAT CACCTCAGAA   180
CCCACTCAGC CTCCACCAAC TTCTCCCCCA TTGGTCCATG ACTCCGACCT TGAACATGTC   240
CTAACCCCCT CCACGTCCTG GACGACCAAA ATACTCAAAT TTATCCAGCT GACCTTACAG   300
AGCACCAATT ACTCCTGCAT GGTTTGCGTG GATAGATCCA GCCTCTCATC CTGGCATGTA   360
CTCTACACCC CCAACATCTC CATTCCCCAA CAAACCTCCT CCCGAACCAT CCTCTT       416
```

HTLV-I PEPTIDE ANTIGENS AND KIT

This application is a continuation-in-part of U.S. patent application for "HTLV-I Peptide Antigen and Methods", Ser. No. 366,313, filed Jun. 13, 1989 now U.S. Pat. No. 5,066, 579, which in turn is a continuation of U.S. patent application for "HTLV-I Peptide Antigen and Methods," Ser. No. 948,270, filed Dec. 31, 1986, now abandoned.

1. FIELD OF THE INVENTION

The present invention relates to an HTLV-I and HTLV-II specific antigens, and to methods of preparing and using the antigen.

2. REFERENCES

Cwirla, S. E., et al., Proc Nat Acad. Sci, USA, 87:6378 (1990).

Huynh, T. V., et al., in "DNA Cloning, Volume 1," ed. D. M. Glover, Washington, D.C.: IRL Press, 1985 (Chapter 2).

Laemmli, U.K., Nature, 227:680 (1970).

Lipka, J. J., et al., J Infect Dis, 162: 353 (1990).

Lipka, J. J., et al., Proceedings of the 43 Meeting (1990).

Maniatis, T., et al., *Molecular Cloning: A Laboratory Manual*, Cold Spring Harbor Laboratory (1982).

Matsushita, S., et al., *Proc Natl Acad Sci* (USA), 83:2672 (1986).

Miyoshi, I, et al., *Nature* 294:770 (1981).

Poiesz, B. J., et al., *Proc Natl Acad Sci* (USA), 77:7415 (1980).

Popovic, M., et al., *Science,* 29: 856 (1983).

Samuel, K. P., et al., Science, 226:1094 (1984).

Samuel, K. P., Gene Anal Tech, 2:60 (1985)

Scott, J. T.<et al., Science, 249:386 (1990).

Seiki, M., et al., *Proc Natl Acad Sci* (USA), 80:3618 (1983).

Shimotokno, K., et al, Proc Nat Acad Sci, USA, 82:3101 (1985).

3. BACKGROUND OF THE INVENTION

The human T-cell leukemia viruses (HTLV) represent a family of T-cell retroviruses with three known members. HTLV type I (HTLV-I) ha transforming activity in vitro and is etiologically linked to adult T-cell leukemia, which is known to be endemic in several parts of the world. HTLV-II is another retrovirus having transforming capacity in vitro, and has been isolated from a patient with a T-cell variant of hairy cell leukemia. HTLV-III, which has also been called lymphadenopathy-associated virus and is now known as the human immunodeficiency virus (HIV), is lytic for certain kinds of T cells and has been linked to the etiology of acquired immunodeficiency syndrome (AIDS). Unlike the HTLV-I and -II viruses, HTLV-III is not known to have in vitro transforming activity.

The diagnosis of HTLV-I infection is usually based on serum antibody response to HTLV-I peptide antigens. This usually involves an initial screening assay to identify HTLV-I antibodies, based on an enzyme immunoassay (EIA) with HTLV-I virion peptides. The assays presently used for blood screening detect about 0.5 to 0.05% HTLV-I and HTLV-II positives; of these, about 4 out of 5 are false positives. Therefore, positive sera must be further tested in a confirmatory assay, using Western blot or radioimmunoprecipitation assays which detect antibody reaction to specific HTLV-I peptide antigens.

Current blood testing procedures require confirmation tests based on immunoreaction with HTLV-I p24 gag protein and at least one of the envelope proteins gp46, gp21, or gp68. When the test antigens are prepared from virion proteins, only gp46 gives a high rate of antibody reaction with true HTLV-I seropositives. Even then, the reaction with gp46 may be detected only by additional antigen testing with a more sensitive radioimmunoprecipitation assay. The above screening and confirmation testing identifies HTLV-I and HTLV-II positives, but does not distinguish between the two HTLV viruses.

It would therefore be desirable to provide an improved method for detecting HTLV-I positive sera. In particular, the improved test should be capable of detecting all HTLV-I and HTLV-II positive sera, with a minimum number of false positives, and also be able to distinguish HTLV-I from HTLV-II positive sera.

4. SUMMARY OF THE INVENTION

It is therefore one object of the invention to provide an improved method and kit for detecting HTLV-I and HTLV-II positive human sera.

Another object of the invention is to provide such method and kit capable of distinguishing HTLV-I and HTLV-II positive sera.

In the above-cited patent application for "HTLV-I Peptide Antigen and Assay," there is disclosed an HTLV-I peptide composed of a region of the HTLV-I gp46 envelope protein which is immunoreactive with the 0.5α monoclonal antibody (Mab) produced by ATCC cell line HB8755 (Matsushita). The cell line HB8755 has been redeposited in the American Type Culture Collection, 12031 Parklawn Drive, Rockville, Md. 20852, and given new ATCC Deposit No. HB10571. The region is contained in a 41 amino acid sequence overlap of three gp46 peptide antigens, designated MTA-1, MTA-4, and MTA-5. The 41 amino acid sequence overlap region contains the sequence Leu-Leu-Val-Asp-Ala-Pro-Gly-Tyr-Asp-Pro-Ile-Trp-Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Leu-Glu-Pro-Ser presented as SEQ ID NO: 2, and may include the additional residues presented as SEQ ID NO: 3 at the C-terminal Ser residue of the 41 amino acid sequence. A common-amino acid sequence in recombinant and synthetic peptides which is immunoreactive with the 0.5α Mab is the sequence presented as SEQ ID NO: 4.

In another aspect, the invention includes a kit for detecting the presence of HTLV-I infection in human serum. The kit includes a solid support on which the gp46 peptide antigen is carried, and a reporter system for detecting the presence of human antibodies bound to the peptide antigen.

In one embodiment, the kit is in an EIA format for screening human sera for HTLVI antibodies. In another embodiment, the peptide antigen is immobilized on a strip, along with one or more confirmatory HTLV-I antigens, in a Western blot format for confirming HTLV-I serum antibodies.

In still another embodiment, the kit includes an HTLV-II specific antigen, defined below, capable of reacting specifically with antibodies from HTLV-II positive sera. The kit allows for specific detection of HTLV-I and HTLV-II positive sera.

Also included in the invention is a method of detecting HTLV-I positive human sera. In this method, test sera is reacted with a peptide antigen which is immunoreactive with anti-HTLVI monoclonal antibody (Mab) derived from ATCC cell line HB8755, (New ATCC NO: HB10571) designated 0.5α Mab. The presence of anti-HTLV-I antibodies bound to the antigen is detected by a suitable reporter-labeled anti-human antibody.

The 0.5α Mab-reactive peptide may be produced by a random-sequence selection method in which a mixture of random-sequence polynucleotids, preferably encoding 5–10 amino acid residues, is introduced into a suitable expression vector, to form a library of random-sequence vectors. The expression products of the library vectors are screened for the presence of an amino acid sequence which is immunoreactive with the 0.5α Mab. The library clone which expresses such an immunoreactive amino acid sequence is then isolated and used for producing the polypeptide encoded by the inserted sequence.

Also disclosed herein is an HTLV-II peptide antigen comprising less than about 50 amino acids derived from HTLV-II envelope protein gp46, and including the immunogenic region formed by the amino acid sequence presented as SEQ ID NO: 5. A common amino acid sequence in recombinant and synthetic peptides which is immunoreactive with HTLV-II antisera has the sequence presented as SEQ ID NO: 7 or the same sequence extended at the Ser C-terminus by the amino acid sequence presented as SEQ ID NO: 8.

The peptide antigen is used in a test kit for detecting the presence of HTLV-II infection in a human serum. The kit includes a solid support which carries the peptide antigen, and a reporter system for detecting the presence of human antibodies bound to the peptide antigen.

These and other objects and features of the present invention will become more fully apparent when the following detailed description of the invention is read in conjunction with the accompanying drawings.

BRIEF DESCRIPTION OF THE DRAWINGS

FIG. 2 shows the HTLV-I coding sequences and corresponding amino acid sequences for a portion of the HTLV-I envelope protein;

FIG. 3 shows amino acid sequences of homologous regions of HTLV-I and HTLV-II gp46 in the region of the peptide antigen of the invention, and peptide sequences of several HTLV-I gp46 peptide antigens (upper part of figure) and HTLV-II peptide antigens (lower part of figure) in accordance with the invention;

FIG. 6 shows the HTLV-II coding sequence, and corresponding amino acid sequence in the region of the gp46 envelope protein from which HTLV-II peptides of the invention are derived.

DETAILED DESCRIPTION OF THE INVENTION

I. Preparing HTLV-I Peptide Antigens

Figure 1A:
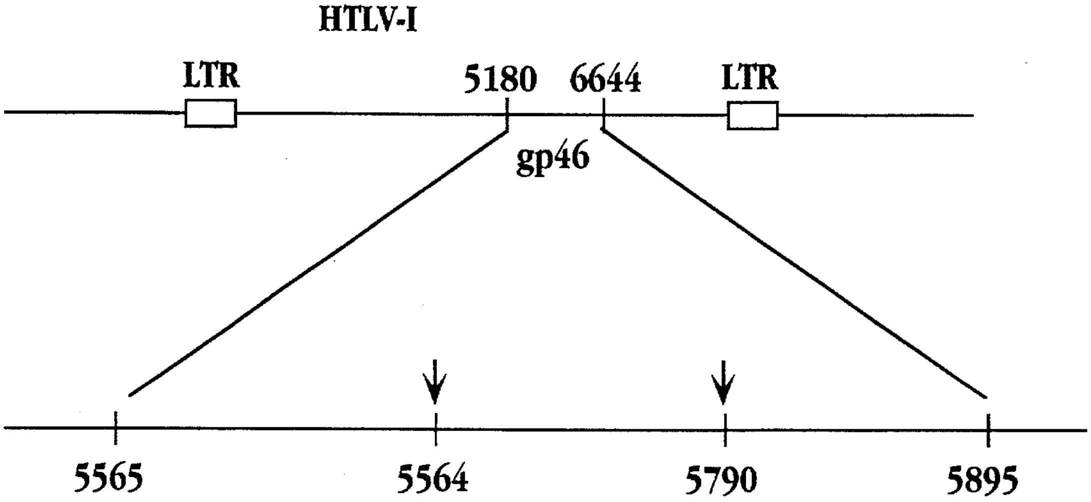
FIG. 1A shows, in the upper line, a portion of the HTLV-I genome containing the gp46 envelope protein coding sequence, and in the lower line, a portion of the gp46 coding region containing the sequences which encode overlapping HTLV-I peptide antigens formed in accordance with the invention, and designated MTA-4, MTA-1, and MTA-5 in FIG. 1B.
Figure 1B:
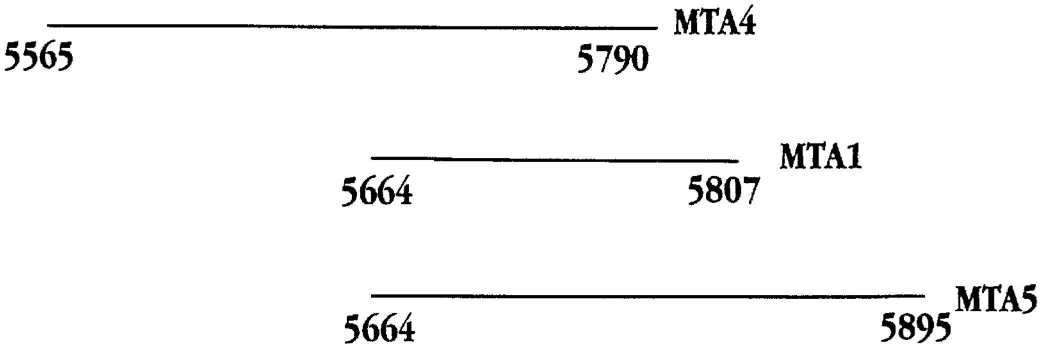

This section describes the preparation of HTLV-I peptide antigens which are immunoreactive with anti-HTLV-I antibodies found in individuals with HTLV-I-related T-cell leukemia. The antigens are prepared using random HTLV-I gene sequences 100–300 base pairs in length cloned in a suitable expression vector, then selected with antibody for expression of immunoreactive peptides.

A. HTLV-I Genomic Libraries

Genomic libraries of HTLV-I are prepared conventionally from cellular DNA containing an HTLV-I proviral genome. Duplex DNA may be prepared from HTLV-I infected cells, including T-cells isolated from patients known to be infected with HTLV-I virus, or known cell lines, such as HUT 102-B2 (Poiesz), MT-2 (Miyoshi), and MJ-tumor (Popovic) cells, all of which have been shown to produce HTLV-I virus. The viral genome is integrated into host DNA in these cells. Methods for preparing cell lines containing the HTLV-I genome are detailed in the above references.

The total host genomic DNA from the above cell line is partially digested with a frequent cutter, such as HaeIII or AluI, under Conditions which produce partial digest fragments in the 15–20 kbase size range, and the digested material is fractionated, for example, by sucrose gradient Centrifugation, to isolate the 15–20 kbase fragments. The fragments are then cloned into a suitable cloning vector, preferably a phage cloning vector which can efficiently incorporate a 15–20 kbase insert. In a preferred method, the isolated fragments are treated with EcoRI methylase, and EcoRI linkers are ligated to their ends under standard conditions (Maniatis), and then cloned into a phage vector, such as λ Charon 4a, having a unique EcoRI insertion site.

The cloned genomic fragments are screened with a probe which is complementary to a selected sequence of the full-copy HTLV-I genome. HLV-I sequences are known (Seiki), as are methods for producing radiolabeled synthetic oligonucleotide probes for selected sequences. In addition, synthetic oligonucleotides of specified sequences can be made by commercial services, such as provided by Synthetic Genetics, Inc. (San Diego, Calif.). Using such an oligonucleotide probe, molecular clones containing HTLV-I sequences are isolated from the library by standard hybridization procedures (Maniatis, p. 322). The clones can first be analyzed by restriction site analysis, to confirm that the full viral genomic sequence is present, as indicated by the presence of direct long terminal repeats which flank the integrated viral genome. The identified molecular clone is digested with a suitable endonuclease to release the full-copy viral genome. A preferred endonuclease for this purpose is SacI, which cuts the viral genome in the long terminal repeats (LTR) at either end of the viral coding sequences, but does not produce internal cleavage. If the clonal HTLV-I genome is a variant with a third SaCI site, an appropriate restriction enzyme will be chosen to isolate the full-length genome. The purified full-copy sequence is about a 9.5 kilobase fragment. Alternatively, a fragment of the genome representing the env gene sequences alone may be purified for production of the expression library.

Alternatively, cloning vectors containing full-copy HTLV-I duplex DNA have been reported (Seiki) and may be obtained directly from the investigators, as indicated in Example 1.

To produce the desired HTLV-I genomic library, the full-copy HTLV-I insert is excised from the above cloning vector, such as by complete digestion with SacI, and isolated as a 9.5 kilobase fragment, as described in Example 1. The isolated full-copy fragment is digested to produce DNA fragments, and preferably random fragments with sizes predominantly between about 100–300 base pairs. Example 1 describes the preparation of such fragments by DNAase digestion. Because it is desired to obtain peptide antigens of between about 30–100 amino acids, the digest fragments are preferably size fractionated, for example by gel electrophoresis, to select those in the approximately 100–300 base pair size range.

The genomic digest fragments are inserted into a suitable cloning vector, preferably an expression vector which permits expression of the coded-for peptide in a suitable host. One preferred expression vector is λgt11, which contains a unique EcoRI insertion site 53 base pairs upstream of the translation termination codon of the β-galactosidase gene. Thus, the inserted sequence will be expressed as a β-galactoidase gene. Thus, the inserted sequence will be expressed as a β-galactosidase fusion protein which contains mos of the N-terminal portion of the β-galactosidase gene, the heterologous peptide, and at least a portion of the C-terminal region of the β-galactosidase gene. This vector also produces a temperature-sensitive repressor (cI857) which causes viral lysogeny at permissive temperatures, e.g., 32° C., and leads to viral lysis at elevated temperatures, e.g., 42° C. Advantages of this vector include: (1) highly efficient recombinant generation, (2) ability to select lysogenized host cells on the basis of host-cell growth at permissive, but not non-permissive temperatures, and (3) high levels of recombinant fusion protein production. Further, since phage containing a heterologous insert produce an inactive β-galactosdase enzyme, phage with inserts can be readily identified by a β-galactosidase colored-substrate reaction.

The digest fragments inserted into the expression vector may be modified, if needed, to contain selected restriction-site linkers, such as EcoRI linkers, according to conventional procedures. Example I illustrates methods for cloning the digest fragments into λgt11, which includes the steps of blunt-ending the fragments, adding EcoRI linkers and ligating the fragments with EcoRI cut λgt11. The resulting viral genome library may be checked to confirm that a relatively large (representative) library has been produced. This can be done, in the case of the λgt11 vector, by infecting a suitable bacterial host, plating the bacteria, and examining the plaques for loss of β-galactosidase activity. Using the procedures described in Example 1, about 60% of the plaques showed loss of enzyme activity, when compared to the level of background phage showing loss of enzyme activity, as seen in Example 1.

B. Peptide Antigen Expression

The genomic library formed above is screened for production of peptide antigen (expressed as a fusion protein) which is immunoreactive with the human anti-HTLV-I antibody of interest. One antibody of particular interest for diagnosing HTLV-I infection is the 0.5α monoclonal antibody (Mab) which, as noted above, is has the same specificity as antibodies present in patients with T-cell leukemia related to HTLV-I infection. The antibody is produced by the EBV-transformed B-lymphocyte cell line having ATCC Deposit No. HB8755 (New ATCC NO. HB10571) (See Example 2).

In a preferred screening method, host cells infected with phage library vectors are plated, as above, and the plate is blotted with a nitrocellulose filter, to transfer recombinant antigens produced by the cells onto the filter. The filter is then reacted with the anti-HTLV-I antibody, washed to remove unbound antibody, and reacted with reporter-labeled, anti-human antibody, which becomes bound to the filter, in sandwich fashion, through the anti-HTLV-I antibody.

Typically, phage plaques which are identified by virtue of their production of recombinant antigen of interest are re-examined at a relatively low density, for production of antibody-reactive fusion protein. The screening procedures described in Example 2 are illustrative. Several recombinant phage clones which produced immunoreactive recombinant antigen were identified in the procedure.

The one or more library vectors identified as above are preferably analyzed by nucleic acid sequencing, to determine the positions of the peptide-coding regions within the HTLV-I genome. Methods for excising the heterologous insert (including adjacent coding sequences of the fusion protein, if desired) from the selected library vectors, and for purifying and sequencing the excised fragments generally follow known procedures, as outlined in Example 3. The coding sequences of three peptides which were found to be immunoreactive with the 0.5α Mab are shown in the drawing. The three heterologous sequences were matched with the known sequence of HTLV-I (Seiki). As discussed more fully in Example 3, all of the sequences fall within base pairs 5565 and 5895 of the HTLV-I genome, within the gene coding for the HTLV-I envelope protein gp46 (drawings, part A), and have an overlapping coding sequence (defined by the two arrows in the drawing) between base pairs 5664 and 5790 (drawing, part B). As seen in the drawing, part C, the overlapping sequence codes for a 41-amino-acid peptide antigen having the following amino acid sequence: Leu-Leu-Val-Asp-Ala-Pro-Gly-Tyr-Asp-Pro-Ile-Trp-Phe-Leu-Asn-Thr-Glu-Pro-Ser-Gln-Leu-Pro-Pr-Thr-Ala-Pro-Pro-Leu-Leu-Pro-His-Ser-Asn-Leu-Asp-His-Ile-Leu-Glu-Pro-Ser presented as SEQ ID NO: 2. Screening studies conducted in support of the invention indicate that the MTA-1 peptide picks up the highest percentage of HTLV-I positive sera, particularly among subjects of Japanese ancestry. As seen in FIG. 3, the MTA-1 peptide includes the additional Ile-Pro-Trp-lys-Ser-Lys residues at the Ser C terminus of the above sequence. In a preferred embodiment of the invention, the HTLV-I specific peptide contains the immunogenic region of the C-terminal 47 amino acid MTA-1 sequence which is immunoreactive with the 0.5α Mab.

More generally, the HTLV-I peptides of the invention include the immunogenic region f the above amino acid sequence which is immunoreactive with the 0.5α Mab. As defined herein, the specified sequence includes minor, neutral amino substitutions which do not appreciably decrease the immunoreactivity of the peptide antigen for the 0.5α Mab. Such amino substitutions may be selected on the basis of similarities in hydrophobicity, size, charge, hydrogen bonding ability, and effect on secondary structure according to known amino acid substitution principles.

The selected clones are used for scale-up production, for purposes of recombinant protein purification. Scale-up production is carried out using one of a variety of reported methods for (a) lysogenizing a suitable host, such as *E. coli*, with a selected λgt11 recombinant, (b) culturing the transduced cells under conditions that yield high levels of the heterologous peptide, and (c) purifying the recombinant antigen from the lysed cells.

In one preferred method involving the above λgt11 cloning vector, a high-producer *E. coli* host, BNN103, is infected with the selected library phage, and replicaplated on two plates. One of the plates is grown at 32° C., at which viral lysogeny can occur, and the other at 42° C., at which the infecting phage is in a lyric-stage and therefore prevents cell growth. Cells which grow at the lower, but not the higher temperature, are therefore assumed to be successfully lysogenized.

The lysogenized host cells are then grown under liquid culture conditions which favor high production of the fused protein containing the viral insert, and lysed by rapid freezing to release the desired fusion protein. These methods are detailed in Example 4.

HTLV-I coding sequences from the λgt11 clone expressing the peptide antigen MTA-1 have been prepared by PCR amplification, as described in Section II below, and cloned into the pGEX-1 expression vector (Pharmacia, Piscataway, NJ). Inserts cloned into pGEX-1 were expressed as a fusion protein with the protein Sj26, which is a 26 Kdal Glutathion S-transferase from the parasite *Schistosoma Japonicum*. Limited paneling of pGEX-MTA-1 against sera from HTLV-I or HTLV-II infected individuals has revealed no significant difference between the reactivity of pGEX-MTA-1 vs β-gal-MTA-1.

C. Peptide Purification

The recombinant peptide is purified by standard protein purification procedures which may include differential precipitation, molecular sieve chromatography, ion-exchange chromatography, isoelectric focusing, gel electrophoresis and affinity chromatography. In the case of a fused protein, such as the β-galactosidase fused protein prepared as above, the protein isolation techniques which are used can be adapted from those used in isolation of the native protein. Thus, for isolation of a-galactosidase fusion protein, the protein can be isolated readily by simple affinity chromatography, by passing the cell lysis material over a solid support having surface-bound anti- galactosidase antibody. This approach is used in Example 4.

II. Peptide Immunoreactivity With 0.5α a MAB

The invention also includes, in another aspect, a method of detecting HTLV-I positive human sera, by reacting sera with a peptide antigen which is immunoreactive with the HTLV-I Mab produced by ATCC cell line HB8755, (New ATCC NO. HB10571) i.e., the 0.5α Mab. The presence of HTLV-I specific antibodies in sera is detected by a reporter-labeled anti-human antibody, as described in Example 7.

A. HTLV-I Derived Peptides

In one embodiment, the peptides contain the immunogenic region from the 41-amino acid overlap region from above-described MTA-1, MTA-4, and MTA-5 HTLV-I peptides. These peptide antigens were further characterized to confirm the location of the immunoreactive region in the 41 amino acid sequence overlap region. The location of the immunoreactive region in the C-terminal portion of the overlap region was suggested by two lines of evidence. First, the 0.5α Mab was reported to react specifically with the HTLV-I envelope protein, i.e., no reaction was observed with HTLV-II or HTLV-III (HIV-1) envelope proteins. It has since been confirmed by the applicants and their co-workers that the gp46 peptide antigens MTA-1 and MTA-4 described above are reactive with HTLV-I but not HTLV-II or HTLV-III antisera (Lipka).

Secondly, a comparison of the amino acid sequence of MTA-1 peptide with the corresponding region in the HTLV-II gp46 protein (FIG. 3) shows substantially greater homology in the N-terminal half of the peptide than in the C-terminal half (the center region of the HTLV-I and HTLV-II sequences seen in FIG. 3). This would indicate that the greatest differences in anti-genicity would be found in the C-terminal half of the peptide region.

Figure 4A:
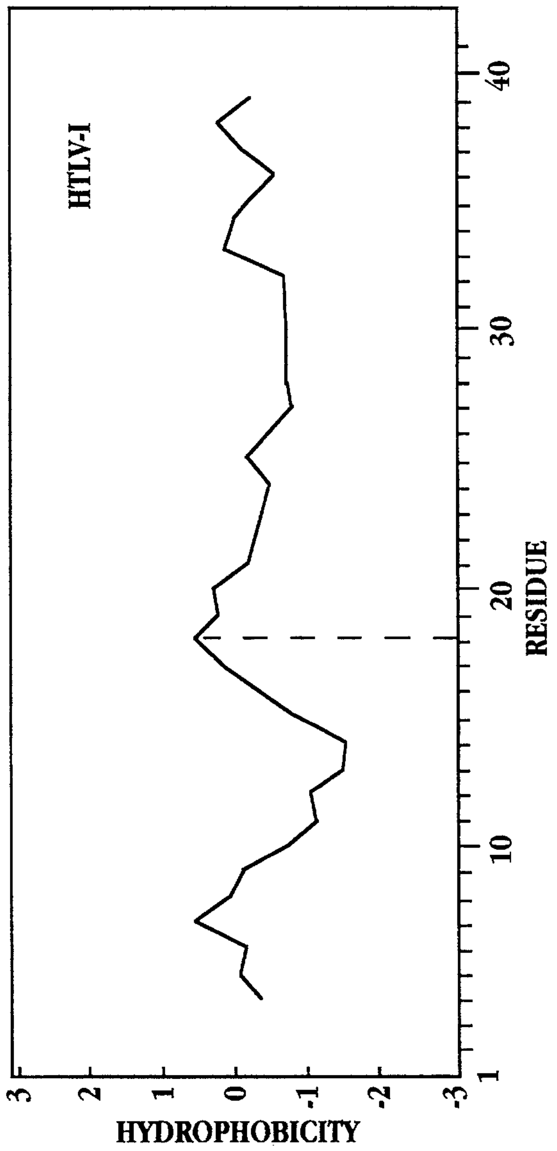
FIGS. 4A and 4B show antigenicity plots for the MTA-1 peptide and corresponding HTLV-II gp46 peptide.
Figure 4B:
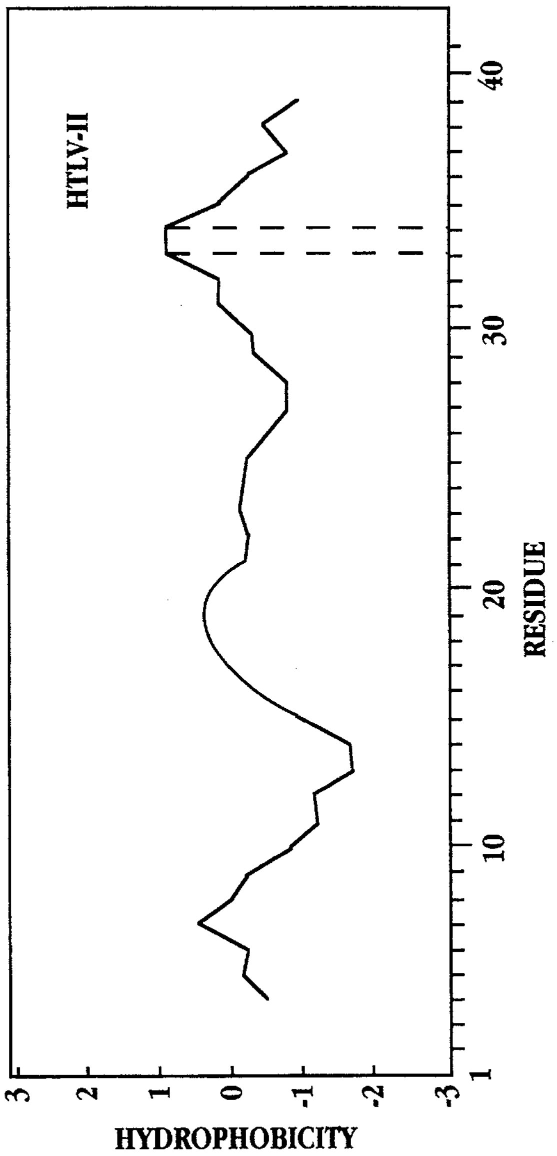

This was further confirmed by antigenicity plots of the two corresponding peptide regions, shown in FIGS. 4A and 4B for HTLV-I and HTLV-II peptides, respectively. The antigenicity plots were generated by a standard hydrophobicity program "Antigen" in PC Gene from Intelligenetics (Palo Alto, Calif.). As seen, the two plots are substantially overlapping in residues 3–28, but diverge markedly in residues 28–40. The divergent residues include the HTLV-I sequence presented as SEQ ID NO: 9.

A number of peptide antigens which include the C-terminal region just indicated were prepared and tested for binding to 0.5α Mab, and to HTLV-I and HTLV-II antisera. The sequences of several of these peptides are indicated in the upper portion of FIG. 3, along with the sequences of the above MTA-1, MTA-4, and MTA-5 peptide antigens. The peptides were prepared by solid-phase synthetic methods, according to standard procedures. Briefly, N-alpha-protected amino acid anhydrides were prepared in crystallized form and used for successive amino acid addition at the N-terminus. At each residue addition, the growing peptide (on a solid support) was acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed.

At each residue-addition step, the amino acid addition reaction may be repeated for a total of two or three separate addition reactions, to increase the percent of growing peptide molecules which are reacted. Typically, 1–2 reaction cycles are used for the first twelve residue additions, and 2–3 reaction cycles for remaining residues After completing the growing peptide chains, the protected peptide resin is treated with liquid hydrofluoric acid to deblock and release the peptides from the support.

The peptides were tested for specific immunoreactivity with 0.5α Mab by binding competition studies, substantially as described in Example 6. The K163 peptide, which contains the 18 C-terminal residues of MTA-4 or MTA-1, strongly inhibits binding of 0.5α Mab to MTA-4. No binding interference, however, was observed with peptide K162, which contains only the 11 C-terminal residues of MTA-4. Peptide K164, which contains the 6 C-terminal residues of MTA-4 and an additional C-terminal 13 residues, weakly inhibited binding between 0.5α Mab and MTA-4 or MTA-1.

These results indicate that the most potent immunoreactive region in the gp46 peptide for the 0.5α Mab is in a region which includes peptide K163, consistent with the divergence in sequence homology and anti-genicity plots between HTLV-I and HTLV-II sequences in this region. The weak binding of 0.5α Mab to the K164 peptide may indicate that the epitope of interest in the presented as SEQ ID NO: 10 region of overlap between K163 and K164, where adjacent N-terminal or C-terminal sequences are required for antigen presentation, or may indicate that the K164 peptide contains an additional epitopic region which is weakly immunoreactive with the 0.5α Mab.

The peptides were also examined for their ability to inhibit binding of antisera from HTLV-I infected patients to MTA-4. In general it was found that the ability of any particular peptide to inhibit binding of 0.5α Mab to MTA-4 paralleled its ability to either bind to HTLV-I antisera in an ELISA binding protocol (Example 6B) or to inhibit binding of human HTLV-I antisera to MTA-4 or MTA-1 in a Western blot assay (Example 8C). Thus, peptide K162 did not react with any HTLV-I sera in the ELIS protocol and did not inhibit binding of J-254 sera to MTA-1 or MTA-4.

B. Random-Sequence Peptides

In another embodiment, the 0.5α Mab-reactive peptide for use in the method is prepared by selection of random-sequence peptides. Recently, it has been demonstrated that antibodies directed against specific short (5–10 residues) peptides can be used to screen libraries of randomly generated peptides for immunoreactive species. (Scott; Cwirla et al). Such a strategy is exploited herein to identify novel sequences which are immunoreactive with the 0.5α monoclonal antibody.

In the preferred method, approximately $10^8$ novel heptapeptides are generated through construction of an epitope library using the filamentous phage fUSE5 as a vector. Other filamentous phage vectors are considered to be equally efficacious in developing such a library.

Figure 5A:
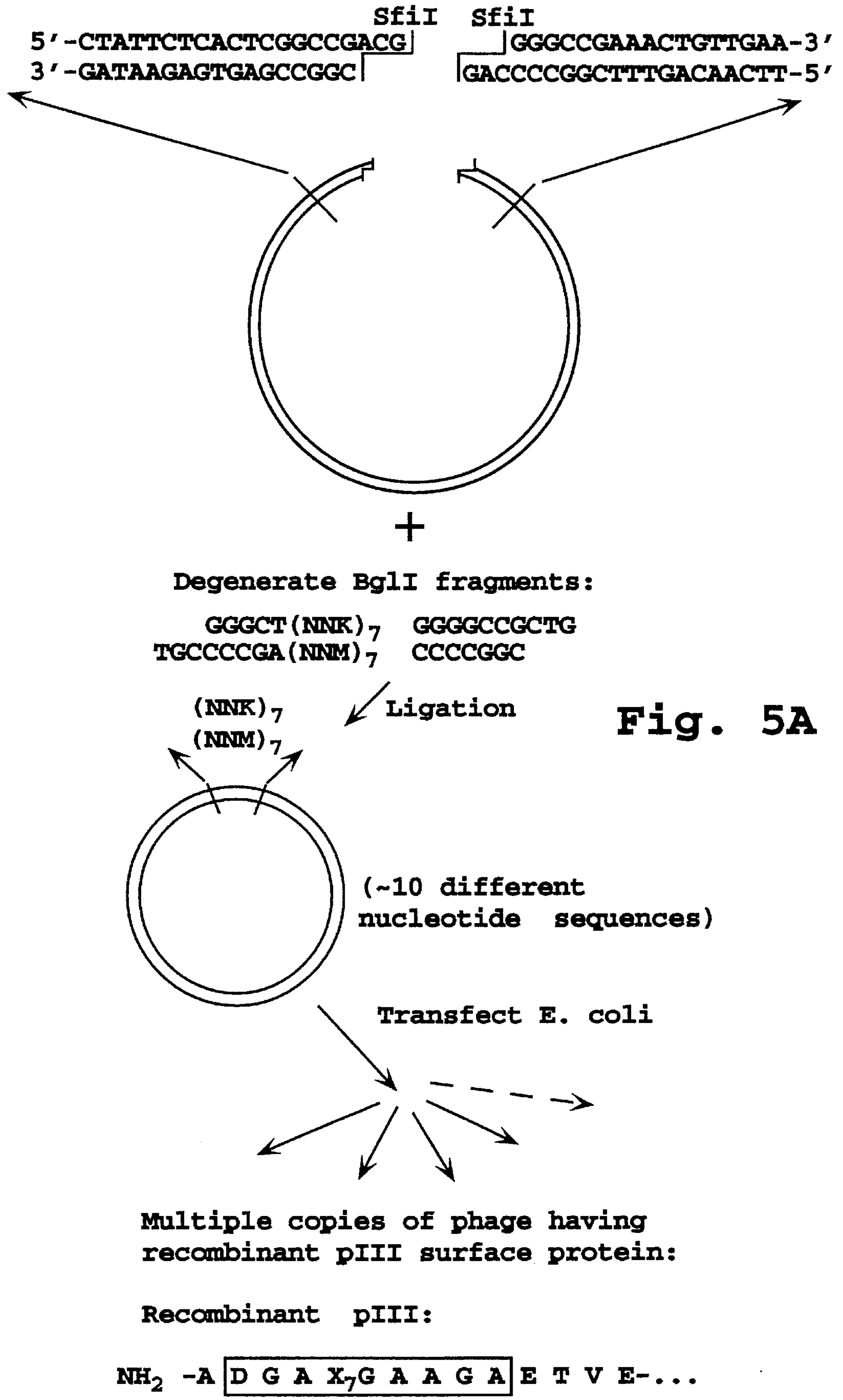
FIG. 5 illustrates recombinant methods for producing and selecting random-sequence peptides, in accordance with the invention.
Figure 5B:
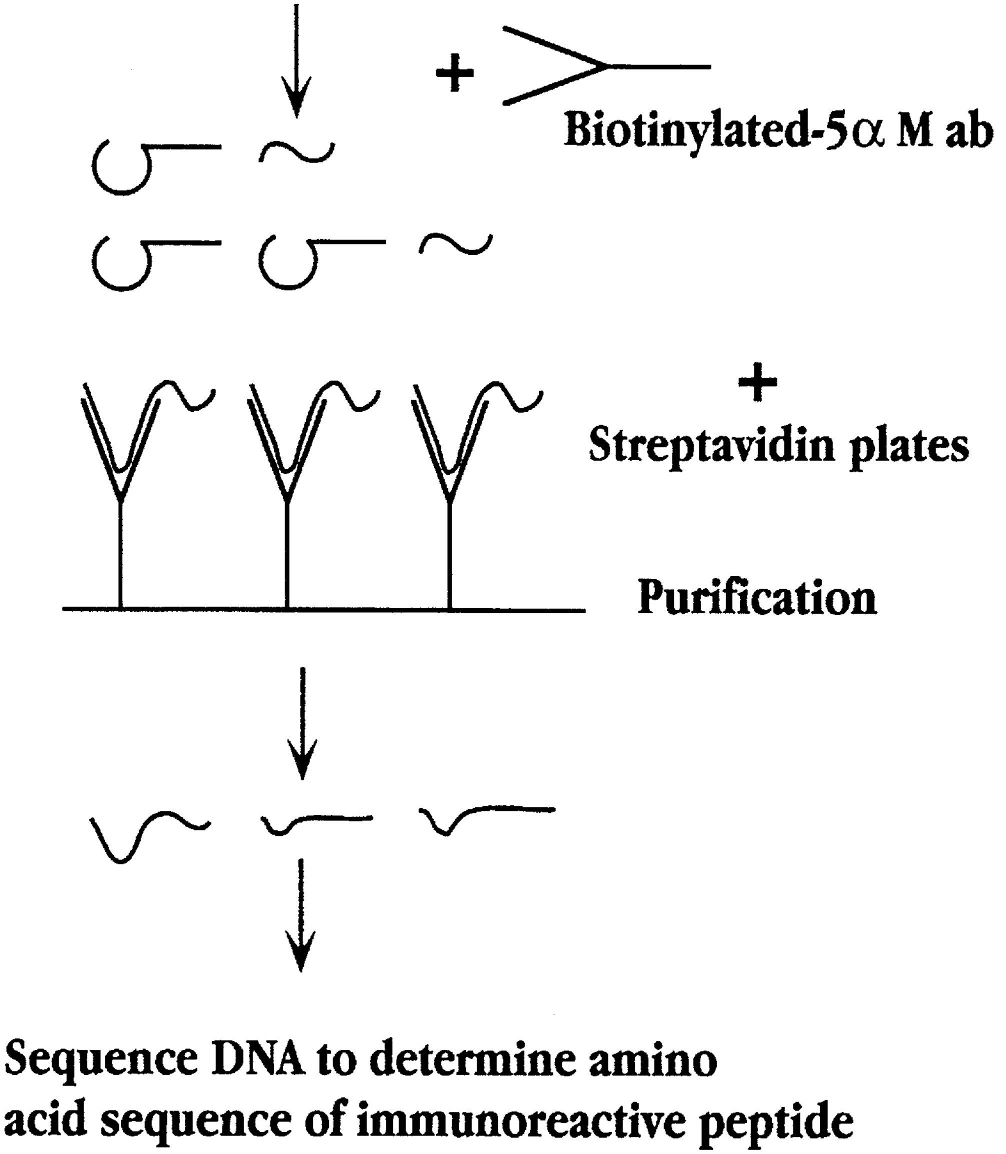
Figure 7:
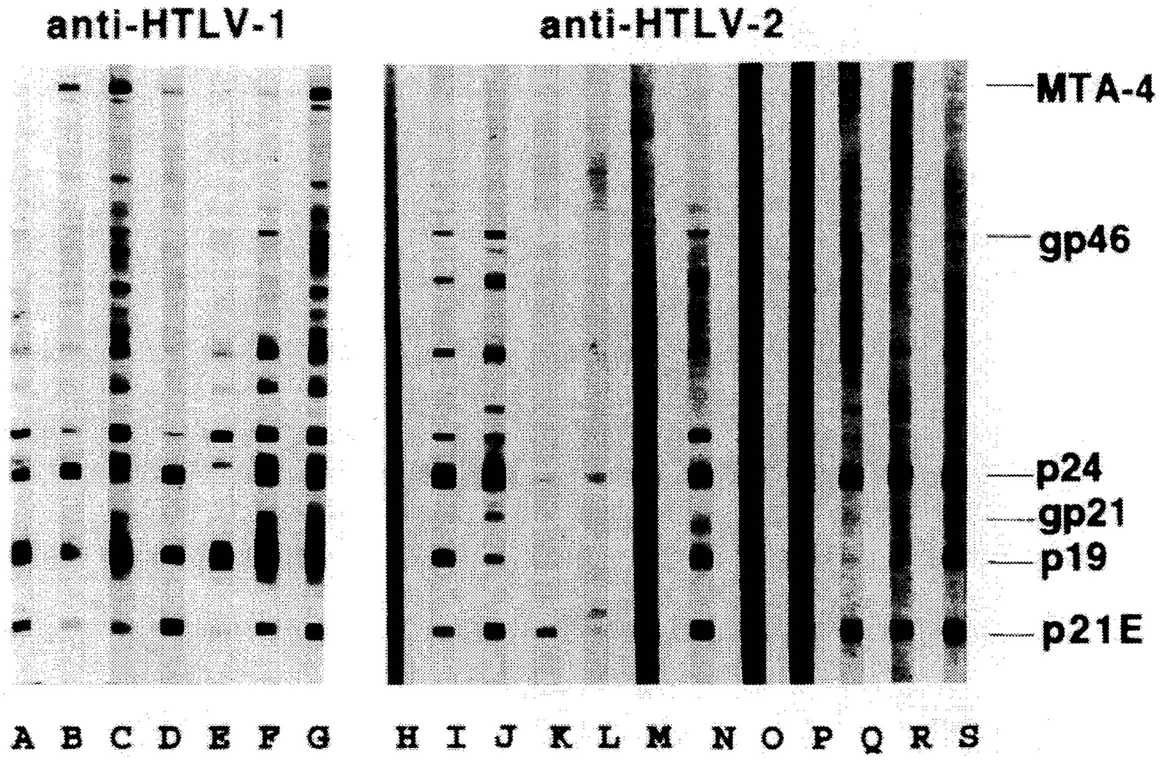
FIG. 7 shows modified Western blots containing HTLV-I viral lysate and recombinant proteins p21E and MTA-4, where lanes A–F and G–R are HTLV-I and HTLV-II antisera, respectively.

FIG. 5 shows schematically the sequence of steps necessary to generate and screen a fUSE5 filamentous phage epitopic library. Briefly, fUSE5 RF DNA is subjected to digestion with restriction endonuclease SfiI to create an insertion site for insertion of foreign DNA. A synthetic (15+3m) base pair (bp) BglI DNA fragment is prepared which contains a degenerate sequence of the form (NNK)m, where N represents A, G, C, or T; K represents G or T; and m can vary from 2 to 15. In the preferred embodiment of the invention, m ranges from 5–10 and the bass are randomly added in single addition events to the template primer. An alternative method of achieving random addition of codons coding for the twenty amino acids is to randomly attach trinucleotide codons representing each amino acid to the template primer.

Following ligation of the insert to the cloning vector, amplification of the filamentous phage vector is achieved by transfection of *E. coli cells*. Successful transfection is measured by the presence of vector borne markers. In the preferred embodiment of the invention, this marker is tetracycline resistance. Recombinant phage are then isolated from bacterial cells. Phage bearing sequences of interest are isolated by an antibody panning method in which phage are incubated with the 0.5α Mab or its Fab fragment. Biotinylated second antibody (goat anti-human IgG) is then added, and complexes Containing biotinylated second antibody, the 0.5α Mab and immunoreactive peptide bearing phage are separated from unreacted antibodies and phage by adhesion onto a streptavidin coated plate. Phage bearing immunoreactive sequences are then eluted, and their DNA sequences are determined.

Foreign DNA sequences present in the filamentous phage fusion protein pIII determine the sequence of the immunoreactive peptide. Peptides discovered to be immunoreactive through this procedure can then be synthesized by standard peptide synthetic methods and prepared as immunogens by conjugation to an appropriate peptide carrier.

III. HTLV-II Peptide Antigens

This section describes the identification and cloning of HTLV-II peptides which are specifically immunoreactive with HTLV-II antisera. The peptides are derived from the HTLV-II gp46 envelope protein region which is homologous to the above described MTA-1 peptide from the HTLV-1 gp46 region.

An HTLV-II peptide desiated GH2-K15 (FIG. 3) corresponding to the HTLV-I peptide MTA-1 was prepared by cloning of an HTLV-II coding sequence corresponding to the desired peptide sequence. A 147 base pair (bp) HTLV-II DNA fragment corresponding to nucleotides 5648 to 5794 of the HTLV-II genome (FIG. 6) was originally amplified from the HTLV-II clone pM04 (which contains the majority of the HTLV-II genome cloned into the BamH I site of the plasmid pBR322) by use of the polymerase chain reaction (PCR) procedure (PerkinElmer/Cetus GeneAmp kit).

The forward direction and reverse primers are indicated in FIG. 6. The amplified DNA was ligated into the EcoR I site of λgt11 phage vector, yielding the clone as3K15 which contains a 147 HTLV-II DNA insert into the -galactosidase gene of the λgt11. The recombinant phage was used to transfect *E. coli* strain BNN103. Details are given in Example 5.

In a preliminary experiment, sera from approximately 200 individuals with pCR-confirmed HTLV-I or HTLV-II infection, as well as sera from approximately 150 uninfected individuals were paneled against the GH2-K15 antigen. 98% of he sera from HTLV-II infected individuals reacted with GH2-K15. None of either the HTLV-I infected sera or the uninfected sera reacted with GH2-K15. The screening results demonstrate that the GH2-K15 peptide is specifically immunoreactive with HTLV-II positive sera.

Several smaller peptides contained with the GH2-K15 amino acid sequence were prepared by recombinant methods, as outlined in Section I. Briefly, the peptides were prepared by PCR amplification of HTLV-II genomic DNA, using PCR primers designed to promote amplification of the sequences indicated, as detailed in Example 5. Five of these peptides, designated (GH2-) K14, K16, K24, K35, and K34 have the sequences shown in FIG. 3.

The recombinant HTLV-II peptides described above were immunoscreened against several HTLV-II and HTLV-I in an ELISA format, as described in Example 8. The results are shown in Table 1. All λgt11 HTLV-II clones except for GH2-K16 were recognized by at least 1 out of the 6 HTLV-II sera tested. GH2-K16, the sole non-reactive clone, is missing the carboxyl terminal 22 amino acids that are included in GH2-K15. All the other clones tested contain at least the 17 amino acids presented as SEQ ID NO: 7 that are present in peptide K125.

Also as seen in Table 1, none of the tested peptides reacted with any of the HTLV-I sera, nor with the 0.5α Mab.

Three of the original HTLV-II clones, GH2-K15, GH2-K35, and GH2-K16 have been cloned into the pGEX-1 expression vector. Recombinant protein expressed by the 3 pGEX-1 HTLV-II clones GH2-K15, GH2-K25, and GH2-K35 have all been recognized by the J-317 HTLV-II serum.

TABLE 1

| | | | HTLV-II ANTIGENS | | | | | |
|---|---|---|---|---|---|---|---|---|
| SERUM | VIRUS | N | K15 | K14 | K16 | K24 | K34 | K35 |
| J-115 | II | 2 | +/– | – | – | – | – | – |
| J-127 | II | 2 | – | – | – | – | – | – |
| J-289 | II | 2 | – | – | – | – | – | – |
| J-309 | II | 2 | – | – | – | – | – | – |
| J-263 | II | 3 | +/– | – | – | + | – | – |
| J-317 | II | 2 | ++ | + | – | ++ | + | + |
| J-103 | I | 2 | – | – | – | – | – | – |
| J-108 | I | 2 | – | – | – | – | – | – |
| J-183 | I | 2 | – | – | – | – | – | – |
| .5α Mab | I | 1 | – | – | – | – | – | – |

A number of peptide antigens which contain amino acid sequences within the K15 Sequence were prepared by solid-phase methods, as outlined in Section III above. The sequences of five of these peptides, designated (GH2-) K169, K170, K125, K126, and K128 are shown in FIG. 3. The peptides were tested for immunoreactivity with several HTLV-I and HTLV-II positive sera, by an ELISA method, and some of the peptides were also examined for their ability to inhibit HTLV-II antibody binding to the K15 antigen.

The K125 peptide was recognized by multiple HTLV-II sera when assayed by ELISA, in one experiment 6 out of 12 HTLV-II sera were able to/bind efficiently to K125. In the same experiment 0 out of 7 HTLV-I sera bound peptide K125. The K125 peptide also inhibited the binding of a strongly reactive HTLV-II sera, J-317, to Western blotted GH2-K15. The ability of sera J-317 to bind GH2-K15 is not affected by incubation with the HTLV-I peptide K163 or the HTLV-II$_i$ peptide K128.

The HTLV-II peptide K170 is recognized by multiple HTLV-II sera in an ELISA based assay, and not recognized by HTLV-I sera in the same assay. The K169 peptide is not recognized by HTLV-II sera in an ELISA based assay.

Data from both the analysis of HTLV-II recombinant antigens and the synthetic HTLV-II peptides indicate that the HTLV-II specific epitope is contained in the 17 amino acid sequence presented as SEQ ID NO; 7 in the GH2-K15 peptide. Data obtained by extensive paneling of the HTLV-I antigens MTA-1 and MTA-4, discussed above, would suggest that the 6 final amino acids of GH2-K15, presented as SEQ ID NO: 8 may also contribute to the epitope recognized by HTLV-II antisera.

IV. HTLV-I and HTLV-II Diagnostic Methods

Three basic types of diagnostic applications of the HTLV-I and HTLV-II peptide antigens of the invention will be described. The first is based on inhibition of complement-mediated, antibody-dependent cytolysis by the peptide. In this method, serum from a test individual is reacted with HTLV-I or HTLV-II infected T-cell clones in the presence of complement. The presence of anti-HTLV-I or anti-HTLV-II antibody is evidenced by cell lysis, as judged, for example, by trypan blue dye exclusion.

Where cell lysis is observed, the specificity of the anti-HTLV-I antibody for the HTLV-I peptide is demonstrated by first reacting the serum with excess HTLV-I or HTLV-II peptide, then mixing the serum with cells in the presence of complement. The presence of HTLV-I or HTLV-II antibody is indicated by a substantial decrease in cell lysis. This method is described in Example 6A.

The method can also be used to quantitate the antibody titer in the analyte serum, by titrating the serum with increasing amounts of peptide, and determining the peptide concentration where a noticeable effect on the extent of cell lysis is first observed.

The second general assay type is an enzyme-immunoassay for screening human sera for HTLV-I or HTLV-II infection. In this assay format, a solid phase reagent having surface-bound HTLV-I or HTLV-II gp46 peptide antigen is reacted with analyte serum, under conditions which allow antibody binding to the peptide on the reagent. After washing the reagent to remove unbound serum components, the reagent is reacted with an enzyme-labeled anti-human antibody, to bind enzyme to the reagent in proportion to the amount of bound anti-HTLV-I antibody on the solid support. The reagent is again washed, to remove unbound antibody, and the amount of enzyme associated with the reagent is determined. One exemplary method, employing an anti-human antibody labeled with alkaline phosphatase, is detailed in Example 7 for a direct HTLV-I screening assay. The enzyme-labeled antibody, and reagents required for enzyme detection, are also referred to herein as reporter means for detecting the presence of human antibody bound to the peptide antigen on the solid support.

The solid surface reagent in the above assay is prepared by known techniques for attaching protein material to solid support material, such as polymeric beads, dip sticks, or filter material. These attachment methods generally include non-specific adsorption of the protein to the support (as in the filter support described in Example 8) or the covalent attachment of the protein, typically through a free amine group, to a chemically reactive group on the solid support, such as an activated carboxyl, hydroxyl, or aldehyde group.

The third general assay type is Western blot assay for use in confirming HTLV-I or HTLV-II antisera. This assay format includes, in addition to the gp46 peptide antigen of the invention, one or more confirmatory HTLV-I or HTLV-II antigens that are effective to detect HTLV-I or HTLV-II antisera. In one preferred format, the confirmatory peptides include the p24 gag protein from HTLV-I viral lysate, and a p21E recombinant envelope protein containing a large portion of the HTLV-I gp21 envelope protein (Samuel, 1984, 1985). The p24 lysate proteins picks up most, but not all HTLV-I and HTLV-II positive sera. The p21E recombinant peptide picks up virtually all HTLV-I and HTLV-II, but also gives some false positives. This modified Western blot assay has been reported by the applicants and co-workers (Lipka). Details of the blot assay procedure are given in Example 8.

As has been described, and as is detailed in Example 8, the modified Western blot format picked up all HTLV-I and HTLV-II positive sera tested (a panel of 95), as evidence by immunoreaction with viral lysate protein p24 and recombinant protein p21E. In addition, the MTA-4 peptide was immunoreactive with confirmed HTLV-I sera only. The modified blot assay thus can be used to confirm HTLV-I or HTLV-II antisera, and to distinguish the two types of HTLV virus by Selective immunoreaction with the peptide of the invention In another embodiment of the Western blot assay, the HTLV-I peptide antigen is replaced by the HTLV-II gp peptide antigen described in Section III. In this format, the HTLV-I viral lysate proteins and p21E recombinant protein provide confirmation i of HTLV-I or HTLV-II antisera, as above. The HTLV-II specific peptide will pick up HTLV-II, but not HTLV-I antisera, and thus provides a positive confirmation of HTLV-II antisera.

The two formats can be combined to include both HTLV-I and HTLV-II specific peptide antigens, to give positive information of either MTLV antisera.

V. Vaccine Compositions

Also included in the invention is a vaccine composition containing an HTLV-I gp46 peptide and a antigen carrier, such as an immunogenic protein, to which the antigen peptide is bound. The peptide contains an immunogenic region formed by he above 41- or 47-amino acid overlap of MTA-1, MTA4, and MTA-5 peptides described in Section I, which is immunoreactive with anti-HTLV-I 0.5α Mab, i.e., the antibody derived from ATCC cell line HB8755 (New ATCC NO. HB10571). More specifically, the peptide contains the immunogenic region of the peptide sequence presented as SEQ ID NO: 4. Since the 0.5α Mab is a neutralizing antibody, the antibody raised by the peptide is expected to be a neutralizing antibody.

The vaccine composition may alternatively include the HTLV-II gp46 peptide containing the HTLV-II specific immunogenic region formed by the amino acid sequence presented as SEQ ID NO: 5, and preferably formed by the amino acid sequence presented as SEQ ID NO: 6, or presented as SEQ ID NO: 7.

Particularly useful protein carriers for the peptide(s) include keyhole limpet hemocyanin (KLH), tetanus toxoid, poly-1-(Lys:Glu), peanut agglutinin, poly-D-lysine, diphtheria toxoid, ovalbumin, soybean agglutinin, bovine serum albumin (BSA), human serum albumin, and the like.

The immunogenic peptide(s) may be conjugated to the carrier by a variety of known methods, including chemical derivatization and by genetic engineering techniques. Such latter technique is disclosed in more detail by Gerald Quinnan, "Proceedings of a Work-shop", Nov. 13–14, 1984. Vaccines and inocula the present invention may be administered by injection, usually intramuscularly or subcutaneously, orally by means of an enteric capsule or tablet, as a suppository, as a nasal spray, and by other suitable routes of administration. For a human patient, a suitable dose of the polypeptide depends, in part, upon the chosen route of administration and a number of other factors. Included among those factors are the body weight of the mammal to be immunized, the carrier when used, the adjuvant when used, and the number of inoculations desired to be used.

Individual inoculations for a human patient typically contain unit doses of about 10 micrograms to about 100 milligrams of polypeptide, exclusive of any carrier to which the polypeptide may be linked. If desired, a series of doses may be administered over a period of time for optimum immunity. Unit dosage forms of the vaccine can also be provided, if desired, containing the aforementioned amounts of the polypeptide.

In any event, the immunogen contained in a vaccine or an inoculum is present in an "effective amount," which amount depends upon a variety of factors as is well known in the immunological arts, eg., the body weight of the mammal to be immunized, the carrier moiety used, the adjuvant used, the duration of protection sought, and the desired immunization protocol.

The following examples illustrate various aspects of the invention, but are in no way intended to limit the scope thereof.

Materials

The materials used in the following Examples were as follows:

Enzymes: DNAase I and alkaline phosphatase were obtained by Boehringer Mannheim Biochemicals (BMB, Indianapolis, Ind.); EcoRI, EcoRI methylase, DNA ligase, and Polymerase I, from New England Biolabs (NEB, Beverly, Mass.); and RNase was obtained from Sigma (St. Louis, Mo.).

Other reagents: EcoRI liners were obtained from NEB; and nitro blue tetrazolum (NBT), 5-bromo-4-chloro-3-indolyl phosphate (BCIP), 5-bromo-4-chloro-3-indolul- -D-Galactopyranoside (X-gal) and isopropyl -D-thiogalactopyranoside (IPTG) were obtained from Sigma.

EXAMPLE 1

Preparation of an HTLV-I Genomic Library Source of Genomic Material

Bacteriophage containing full-copy DNA insert derived from the HTLV-I genome was obtained from Drs. R. C. Gallo and F. Wong-Staal of the Laboratory of Tumor Cell Biology, National Institutes of Health (Bethesda, Md.). The bacteriophage was digested to completion with SacI, releasing the viral genome, insert. The digested material was electrophoresed on standard 1% agarose gel, and the 9.5 kilobase fragment obtained by electroelution was extracted with phenol/chloroform before ethanol precipitation.

The purified genomic DNA was suspended in a standard digest buffer (0.5M Tis HCl, pH 7.5; 1 mg/ml BSA; 10 mM $MnCl_2$) to a concentration of about 1 mg/ml, and digested with DNAase I at room temperature for about 5 minutes. These reaction conditions were determined from a prior calibration study, in which the incubation time required to produce predominantly 100–300 basepair fragments was determined. The material was extracted with phenol/chloroform before ethanol precipitation The genomic fragments from above were blunt-ended with DNA Pol I under standard conditions (Huynh), then extracted with phenol/chloroform and precipitated with ethanol. The blunt-ended material was ligated with EcoRI linkers, under standard conditions (Maniatis, pp. 396–397), then digested with EcoRI to remove redundant linker ends. The material was then agarose-gel-fractionated to remove non-ligated linkers and to size-select (see below).

The resultant fragments from the previous step were analyzed by electrophoresis (5–10V/cm) on 1.2% agarose gel, using X174/HaeIII and /HindIII size markers. The 100–300 bp fraction was eluted onto NA45 strips™ (Schleicher and Schuell), which were then placed into 1.5 ml microtubes with eluting solution (1 M NaCl, 50 mM arginine, pH 9.0), and incubated at 67° C. for 30–60 minutes. The DNA, now in solution, was extracted with phenol/chloroform and precipitated with ethanol. The pellet was resuspended in 20 μl TE (0.01 M Tris HCl, pH 7.5, 0.001 M EDTA).

λgt11 phage vector (Huynh) was obtained from Promega Biotec (Madison, Wis.). This cloning vector has a unique EcoRI site 53 base pairs upstream from the β-galactosidase translation termination codon. The genomic fragments from above were introduced into the EcoRI site by mixing 0.5–1.0 μg EcoRI-cleaved gt11, 0.5–3 μl of the above HTLV-I genomic fragments, 0.5 μl 1 10×X ligation buffer (above), 0.5 μl ligase (200 units), and distilled water to 5μ. The mixture was incubated overnight at 14° C. followed by in vitro packaging, according to standard methods (Maniatis, pp. 256–268).

The packaged phage were used to infect *E. coli*, strain KM392, obtained from Dr. Kevin Moore, DNAX (Palo Alto, Calif.). Alternatively, *E. coli*, strain Y1090, available from the American Type Culture Collection (ATCC #37197), could be used. The infected bacteria were plated and the resultant colonies were checked for loss of β-galactosidase activity (clear plaques) in the presence of X-gal using a standard X-gal substrate plaque assay method (Maniatis). Table 2 below shows the number of recombinant (clear) plaques obtained with insertion of the EcoRI -ended HTLV--I fragments (row 1 ). An EcoRI linker control (row 2) and vector alone (row 3) were also run. As seen, about 50% of the phage plaques showed loss of enzyme (recombination). The background levels either in the presence or absence of EcoRI linkers were less than 15%, indicating the successful generation of an HTLV-I epitope library. The page libraries contained about $10^6$ plaque-forming units (pfu)/ml.

TABLE 2

| | Insert | Vector | Clear/Total | % Rec |
|---|---|---|---|---|
| 1. | SacI in 3.25 μl | 1 μl | 100/200 | 50 |
| 2. | EcoR1 linker 3.25 μl | 1 μl | 25/178 | 14 |
| 3. | Control | 1 μl | 50/400 | 13 |

EXAMPLE 2

Screening for gp46 Coding Inserts

Purified 0.5 antibody derived from a human cell line (ATCC #HB8755) (New ATCC NO. HB10571) was provided by Dr. Samuel Broder of the National Cancer Institute, National Institutes of Health (Bethesda, Md.). Mouse anti-human IgG antibody covalently derivatized with alkaline phosphatase was obtained from Promega Biotec (Madison, Wis.).

A lawn of KM392 cells infected with about $10^4$ pfu of the phage stock from Example 1 was prepared on a 150 mm plate, and incubated, inverted, for 5–8 hours at 37° C. The lawn was overlaid with a nitrocellulose sheet, causing transfer of HTLV-I recombinant protein from the plaques to the paper. The plate and filter were indexed for matching corresponding plate and filter positions.

The filter was washed twice in TBST buffer (10 mM Tris, pH 8.0, 150 mM NaCl, 0.5% Tween 20), blocked with AIB (TBST buffer with 1% gelatin), washed again in TBST, and incubated overnight after addition of 0.5 monoclonal antibody (diluted to 1–2 μg/ml in AIB, 12–15 ml/plate). The sheet was washed twice in TBST, then contacted with enzyme-labeled anti-human antibody, to attach the labeled antibody at filter sites containing antigen recognized by the 0.5 antibody. After a final washing, the filter was developed in a substrate medium Containing 33 μl NBT (50 mg/ml stock solution maintained at 5° C.) in 5 ml of alkaline phosphatase buffer (100 mM Tris, 9.5, 100 mM NaCl, 5 mM $MgCl_2$). Reacted substrate appeared at points of antigen production, as recognized by the 0.5α Mab.

The areas of antigen production determined in the previous step were replated at about 100–200 pfu on an 82 mm plate. The above steps, beginning with a 5–8 hour incubation, through NBT/BCIP development, were repeated in order to identify plaques which secreted an antigen capable of reacting with the 0.5α Mab. The identified plaques were picked and eluted in phage buffer (Maniatis, p. 443). Three of the recombinent phage plaques which secreted an antibody-reactive peptide were selected for sequencing analysis, according to the procedures in Example 3. The corresponding infected phage has been designated MTA-4, MTA-1, and MTA5.

EXAMPLE 3

Phage Purification and pNA Extraction

Phages MTA-4, MTA-1, and MA-5 were isolated from the plate cultures of the infected *E. coli* Y1088 bacteria. These cells are available from the ATCC (ATCC #31195). The phage was collected by addition of phage-dilution buffer (maniatis) late material was purified from bacterial debris by low-sped centrifugation, and the supernatant was poured into SW 27 tubes. RNase and DNAse were each added to a concentration of 1 μg/ml each from stock solutions of 1 μmg/ml. The sample was incubated for 30 minutes at 37° C., and an equal volume of a polyethylene glycol (PEG), 5.8 g NaCl, 2.0g $MgSO_4.7H_2O$, 1M Tris Cl, pH 7.5, and 2% gelatin was added. The sample was placed in an ice bath for 1 hour to allow the phage particles to form a precipitate, which was then isolated by centrifugation at 10 k for about 20 minutes at The supernatant was decanted, and the pellet was resuspended in 0.6 ml PDB buffer (5.8 g NaCl, 2.0 g $MgSO.7H_2O$, 50 ml 1M Tris Cl, pH 7.5, and 5 ml 2% gelatin) and transferred to 0.5 ml polypropylene microtubes. 5 μl 10% SDS, 5 μl 0.5M EDTA, and 2.5 μl proteinase K (20 mg/ml) were added, and the samples were incubated at 50° C. for 15 minutes.

The detergent and enzyme-treated material was extracted with an equal volume of phenol/chloroform, and centrifuged to ensure separation of the phases. The aqueous phase was transferred to a new tube, and the extraction/centrifugation procedure was repeated with a mixture of chloroform and isoamyl alcohol. An equal volume of isopropanol was added, and the same was inverted several times to mix, and cooled to −70° C. for 20 minutes. The sample was centrifuged for 5 minutes and the supernatant was decanted. The pellet was washed in 70% ethanol, briefly dried in a 37° C. heat block, and resuspended in 100 μl TE buffer, pH 7.5.

The isolated phage DNA was digested with KpnI and SacI and then combined with KpnI/SacI cut plasmid vector pGEM-3 (Promega Biotec) to isolate a plasmid recombinant with the insert of interest. The HTLV-I insert was then sequenced using the standard dideoxy sequencing procedure and forward and reverse primers for λgtl sequences flanking the EcoRI insertion site.

The figure shows the coding sequence and corresponding amino acid sequence of a portion of the fused protein formed by the above methods, for each of the three fused peptides examined. A terminal G base of the β-gal gene and the adjacent CC bases of the env gene contributed by each of the three insert sequences yield a GCC (Ala) codon, replacing the Ser codon which normally occurs at that codon position of all three env inserts. As shown, the insert in the MTA-4 includes a 225 base pair sequence extending from base 5564 to 5790 of the HTLV-I coding region. The insert of the MTA5 phage begins at base 5664, and extends to base 5895. The 231 basepair sequence covers amino acids 162 to 240 of the gp46 protein.

The region of insert overlap, from 5664 to 5790, includes the 42 amino acid sequence from amino acids 162 to 203 of the native gp46 protein.

EXAMPLE 4

Isolation of HTLV-I Peptide Antigens

A. Construction of Lysogens

EcoRI, strain C600, was obtained from Dr. R. Davis, Stanford University (Stanford, Calif.). Alternatively, EcoRI Y1089 (ATCC #37196) can be used. A 1 ml saturated, overnight culture of the cells was infected with one of the three phages from Example 3 by adsorbing 10 μl of eluted plaque stock to 50 μl of overnight bacterial culture. The infected bacteria were spread only LB agar plates (Maniatis, p. 440) and incubated at 32° C. The individual colonies were picked with sterile toothpicks onto corresponding grids on two separate plates. One of the plates was incubated at 32° C., and the other at 42° C. Cells that grew at the lower temperature (indicating a lysogenic state produced by the presence of the phage repressor protein) but not at the higher temperature (because of cell lysis) were assumed to be lysogenic. Many lysogenic colonies from each of the three phage types were found.

B. Recombinant Antigen Induction from Lysogens

This Example describes induction of a recombinant protein containing the HTLV-I iepitope from the λgt11 lysogens prepared in Example 4 With the MTA-4 phage. As indicated above, the antigen is produced in the form of a -galactosidase fusion protein which also contains an N-terminal portion of the phage -gal protein.

A superbroth was prepared containing 35 g bactotryprone, 2 g bacto-yeast extract, 5 g NaCl, and 5 ml 1N NaOH in 11 dHO. 500 ml of the superbroth were inoculated 1:100 with a saturated overnight culture of the EcoRI λgt11 lysogens prepared in the previous example. The culture was incubated to $A_{600}$≈0.4–0.5 with vigorous aeration.

In order to maximize protein production, the temperature of the culture was raised to 43°–44° C. thereby inactivating the temperature-Sensitive -galactosidase repressor gene. The temperature was maintained at 43° C. with a 65° C. water bath for 15 minutes with aeration. IPTG, which induces -galactosidase expression by competitively binding to the -galactosidase repressor, was added to the broth to 2 mM to further increase protein production. The culture was returned to the 38° C. shaker for about an hour. The cells were then pelleted at 6,000×g for 15 minutes at 37° C., resuspended in lysis buffer (10 mM Tris, pH 7.4, 2% Triton X-100, 1% aprotinin, and 50 µg PMSF) and immediately plunged into liquid $N_2$. Lysis was completed upon thawing of the frozen samples.

C. Purification of Fusion Protein

The cell lysate obtained in the previous Example was thawed and warmed to 37° C. 10 µl DNAse (1 µg/ml) was added, and the mixture incubated until the viscosity decreased. The lysate was quickly chilled on ice, clarified t 4° C. for 5 minutes in a microfuge, and loaded onto a 6 ml column of anti- -galactosidase coupled to Sepharose 4B (Pharmacia). The column was allowed to equilibrate 1–2 hour, and washed with 7 volumes (column volumes) of TX buffer (10 mM Tris, pH 8.0, 2% Triton X-100, 50 µg/ml PMSF), followed by 2 volumes of 5 mM 3,5-diiodosalicylic acid in TX buffer. Fusion protein was then eluted from the column with 35 mM 3,5-diiodosalicylic acid in TX buffer. The majority of protein was eluted in the first 3–4 volumes, and removal was substantially complete after 7 volumes.

The eluted samples were desalted and concentrated using Amicon filters (Danvers, Mass.).

EXAMPLE 5

Preparing HTLV-II Antigens

A. Synthesis and Cloning of HTLV-II DNA Sequences

The polymerase chain reaction (PCR) procedure was used to generate HTLV-II DNA sequences for cloning. Six 30 bp DNA primers were synthesized. All 6 primers had 3 bp of gt11 sequence followed by an EcoR I site at their 5' ends. This was followed by 21 bp of HTLV-II sequences. The 3 forward direction primers contained HTLV-II sequences corresponding to nucleotides 5648–5668, 5687–5707, and 5726–5745. The 3 reverse direction primers contained HTLV-II sequences corresponding to nucleotides 5794–5774, 5776–5756, and 5728–5708.

PCR was performed according to the manufacturers instructions (Perkin Elmer/Cetus), and all PCR reactions contained 2 ng of the above HTLV clone as template and 1 µM of the appropriate PCR primers PCR amplification was carried out for 25 cycles. Each cycle involved template denaturation for 1 minute at 94 deg. C., annealing of primer to template for 2 minutes at 50 degC., followed by primer extension for 2 minutes at 72 ged. C. Afterwards the amplified DNA was purified and then digested to completion with EcoRI. The digested DNAs were then ligated into the EcoRI site of lambda gt11. The recombinant phage DNAs were then packaged and the frequency of non-recombinant phage was determined by plating in the presence of 5-bromo-4-chloro-3-indolyl β-D-galactopyranoside.

The ratio of recombinant to non-recombinant phage was about 50/1. Multiple isolated plaques from each of the 6 recombinant phage clones were picked and subsequently screened using PCR with lambda gt11 flanking primers 11F and 11R, and/or the HTLV-II plaques described above. Clones containing correctly sized and orientated inserts were then amplified and used in subsequent immunoscreening assays. The EcoR I fragment from 3 of the clones GH2-K15, GH2-K16 and GH2-K35 were subsequently subcloned into the pGEX-1 plasmid and DNA sequenced. The sequences obtained perfectly matched the reported sequence for the desired region of HTLV-II (Shimotokno).

B. Immunological Analysis of MTLV-II Clones

Recombinant phage was mimed 1/1 with wild type gt11 and used to infect *E. coli* strain KM-392. After allowing the phage to grow for ~5 hours expressed proteins were bound to nitrocellulose filters overnight. Filters were subsequently washed 3×with TBS (0.5 M NaCl, 20 mM Tris Ph 8.0), cut into sections, and blocked using TBS plus 1% Gelatin. Filter sections were then incubated overnight with 1st stage antibody, usually sera from HTLV-I or HTLV-II infected individuals diluted 1/100 in TBS plus gelatin. After washing with TBS, the filters were incubated with alkaline phosphatase conjugated goat anti human sera for at least 1 hour. The filters were washed with TBS and bound antibody was then detected by incubating the filters in a solution of nitroblue tetrazolium chloride and 5-bromo-4-chloro 3-indolylphosphate. A particular sera was scored as positive if plaques derived from the recombinant phage could clearly be distinguished from plaques of wild type gt11.

C. Expression and Purification of Recombinant Antigen

β-galactosidase fusion proteins were expressed by first generating lysogens.

Recombinant gt11 phage was used to infect *E. coli* strain BNN103, and lysogens were identified by growing duplicate plates at 32° C. and 42° C. The production of fusion protein was induced by raising the temperature of a log phase culture of lysogen to 42° C. for 15 minutes. Isopropyl thiogalactoside was then added to a final concentration of 1.6 Mm and the cultures were grown for an additional 1 hour at 37° C. Cells were then pelleted by centrifugation at 5000 ×g for 15 minutes and resuspended in 1/50th original culture volume of lysis buffer (2% Triton X-100, 1% Aprotinin, 10 mM Tris, pH 7.4). The solution was then frozen by immersion in a dry ice / ethanol bath and then thawed. DNase I was added to a final concentration of 1 Ng/ml and the lysate was then incubated for 5 minutes at room temperature. Insoluble debris was then pelleted by centrifugation at 10,000 ×g for 10 minutes. The supernatant was then centrifuged as before, sodium dodecyl sulfate-polyacrylamide gel electrophoresis (SDS-PAGE, Lammeli) analysis of aliquots of the pellet and supernatant fractions indicated that GH2-K15 was found primarily in the supernatant fraction.

The supernatant fraction was then combined with 2 mls of Protosorb LacZ adsorbent (Promega) and incubated for 2 hours at 25° C. with agitation. The column resin was then poured into a disposable column and washed with 2× with 10 mls of TX buffer (1% Aprotinin, 10 mM Tris pH 7.4). Bound protein was eluted 14 mls of pH 10.8 carbonate buffer and 2 ml fractions were collected into tubes already containing 1 ml of 2 M tris buffer (pH 7.5). Fractions were then concentrated using Centricon 30s (Areicon) following manufacturers instructions. The fractions were washed with 2 mls of MTBS buffer (150 mM NaCl, 4 mM NaH2PO4, 16 mM Na2HPO4, pH 7.3 ) and then concentrated again.

The location, yield and purity of the purified fusion protein was determined sing SDS-PAGE. After one pass through the immunoaffinity column GH2-K15 recombinant antigen was ~70 % pure. Fractions containing fusion protein were pooled and aliquots of the pool were used in subsequent western blot experiments. Western blot analysis was performed essentially as described previously (Lipka). Titration experiments determined that the optimum loading of purified GH2-K15 antigen was 3 Ng protein/cm nitrocellulose. Peptide competition experiments are described in Example 6C. Nitrocellulose strips containing blotted antigen were then added to the serum samples and incubated and developed as normal.

D. HTLV Antisera

Sera samples were obtained from HTLV-I, HTLV-II, or ELISA reactive—HTLV negative individuals. These samples were from multiple different sources and geographic areas. Many of the seropositive sera samples were also typed for HTLV-I or HTLV-II infection using PCR with strain specific DNA primers. HTLV-I sera samples included 58 PCR proven samples consisting of 45 samples from Jamaican food handlers, 2 intravenous drug users (IVDU) from the New Orleans area, and 11 northern California blood donors. In addition a total of 238 HTLV-I sera samples were obtained from Japan. For the Japanese samples PCR data was unavailable and the infection was typed by western blot analysis of the sera samples against HTLV-I antigens using previously described criteria (Lipka et al. JID). HTLV-II sera samples included 57 PCR proven Samples consisting of 6 IVDU from the New Orleans area, 24 IVDU from the northern California area, and 27 blood donors from the northern California area. HTLV negative Sera included 1 Jamaican food handler, 15 California blood donors, and 29 samples from Japan. PCR analysis of serum samples was performed as described (Lipka).

EXAMPLE 6

Detecting Peptide Antigen Immunoreactivity

A. Inhibition of Cell Lysis

HUT 102-B2 cells were obtained from Dr. R. C. Gallo, LTCB, NIH. This is a long-term cultured T-cell line known to produce HTLV-I.

0.5α antibody (≈5 μg/ml IgG) or a control isotyped matched human IgG was preincubated with MTA-4 recombinant peptide or irrelevant recombinant for 30 minutes at room temperature. 50 μl of these mixtures was then added to $5\times10^5$ HUT 02B2 cells in 96-well micro titer plates, and incubated for 30 minutes at room temperature. 30 μl of rabbit complement per well was added, and incubated 1 hour at 37° C. Cell viability was determined by microscopic examination. Cell lysis was visibly inhibited by addition of the MTA-4 peptide antigen, but not by preincubation with irrelevant recombinant peptide antigen. Isotyped matched human IgG, after preincubation with either recombinant antigen or irrelevant recombinant peptide antigen, had no effect on HUT 102-B2 viability.

B. ELISA Assay

HTLV-I and HTLV-II peptides were examined in an ELISA assay to determine the ability of sera from HTLV infected individuals to bind to the synthetic peptides described above. Briefly, the ELISA assay involved binding a fixed amount of synthetic peptide to a microtiter plate, followed by the addition of sera from a HTLV infected individual. Unbound sera was then washed away and antibody bound to the peptide was detected by a 2nd antibody. The 2nd antibody is conjugated to an enzyme that converts a colorless substrate to a colored product. The amount of colored product produced indicates the amount of serum antibody which bound the peptide. The signal obtained from a particular sera against bound peptide was subtracted from the signal obtained by the sera from a well/which did not contain any peptide. The values obtained after subtraction of the minus peptide background had to be 2.5 times the background value to be considered positive.

C. Antibody Binding Inhibition

The inhibition assay involves the incubation of a large excess of a synthetic peptide with sera from an HTLV infected individual prior to placing a strip of nitrocellulose which contains a HTLV-I or HTLV-II recombinant antigen blotted on to it. If the sera can bind to the peptide, the vast excess of peptide in solution with the antibody will prevent significant binding of the antibody to the relatively small amount of antigen present on the nitrocellulose strip. The amount of antibody bound to the recombinant antigen on the nitrocellulose strip is determined using an enzyme conjugated second antibody in a manner analogous to that described above for the ELISA assay. Control experiments involved incubating HTLV-I sera with the HTLV-II peptide K125 or HTLV-II sera with an HTLV-I peptide, and then determining the ability of the sera to recognize the appropriate recombinant antigen.

EXAMPLE 7

EIA Assay

Purified MTA-4 peptide antigen was prepared as in Example 4, and dot blotted on nitrocellulose filters, which were then used in a solid-phase assay for determination of serum antibodies in patients with T-cell leukemia (6 patients with HTLV-I infection). In each case, 0.1 ml of various serum dilutions, ranging from 1:100 to 1:50,000, from the test individual was added to the filter, and allowed to rest at room temperature for 30 minutes. The filter was the washed two times with TBST buffer (Example 2), and incubated with anti-human antibody conjugated with alkaline phosphatase, as in Example 2. The presence of antibody was determined by color development in NBT and BCIP,i also as in Example 2.

Example 8

Modified Western Blot for Confirming HTLV-I Positive Sera

Recombinant MTA-1 was prepared as in Example 4. Recombinant p21E was prepared as described previously (Samuel, 1984, 1985). HTLV-II viral lysate was prepared from chronically infected cell line MT-2 (Hillcrest Biologicals, Cypress, Calif.). These HTLV-I antigens were combined and then separated under reducing conditions on a 11.5% acrylamide SDS/PAGE gel CLaemli). The resolved proteins were electro blotted onto a nitrocellulose (onto a nitrocellulose membrane blocked with BLOTTO™ (5% nonfat dry milk, 2.5% normal goat serum in 100 mM Tris-HCl, pH 7.4), air dried, and cut into 3 $m_m$ wide strips.

In the assay, the test strips from above were first rehydrated in TBS buffer, and the strips were incubated overnight with human test sera, diluted 1:50 in BLOTTO™. The strips were washed several times with wash buffer, then incubated for one hour with goat anti-human IgG conjugated to alkaline phosphatase (Bio-Rad, Richmond, Calif.). After washing, color development was achieved by incubating the strips in a substrate solution containing 5-bromo-4-chloro-3-indolyl phosphate and nitroblue tetrazolium in 100 mM Tris-HCl buffer, pH 9.5, 50 mM $MgCl_2$. Color development was continued until a uniform background developed on the strip and was halted by rinsing the strips two times with de-ionized water.

A panel of HTLV-I or HTLV-II positive sera were tested. These had been previously confirmed as HTLV-I or HTLV-II positive by PCR analysis (Lipka). The results are shown in FIG. 6, where panels A-G are HTLV-I antisera, and panels H-S are HTLV-2 antisera. Viral lysate protein gp24 was immunoreactive with every serum sample, as was the recombinant peptide gp21E. MTA-4 was immunoreactive with HTLV-I serum samples only.

While the invention has been described with reference to particular embodiments, methods of construction, and uses, it will be clear to those in the are that various other uses, formulations, and methods of practice are within the contemplation of the present invention.

What is claimed is:

1. A peptide antigen comprising less than 77 amino acids derived from HTKV-I envelope protein gp46, said peptide antigen containing the amino acid sequence Leu-Leu-Val-Asp-Ala-Pro -Gly-Tyr-Asp-Pro-Ile-Trp-Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Leu-Glu-Pro -Ser-Ile-Pro-Trp-Lys-Ser-Lys- presented as SEQ ID NO: 1 which is immunoreactive with anti-HTLV-I monoclonal antibody derived from ATCC cell line HB10571.

2. A kit for detecting the presence of HTLV-I infection in a human serum, comprising a solid support with an immobilized gp46 peptide antigen comprising less than 77 amino acids derived from MTLV-I envelope protein gp46, said peptide antigen containing the amino acid sequence Leu-Leu-Val-Asp-Ala-Pro-Gly-Tyr-Asp-Pro-Ile-Trp-Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile-Leu-Glu-Pro-Ser-Ile-Pro-Trp-Lys-Ser-Lys presented as SEQ ID NO: 1 which immunoreactive with anti-HTLV-I monoclonal antibody derived from ATCC cell line HB10571, and said solid support constructed to permit serum antibodies to contact with the peptide antigen, when such serum is applied to the solid support, and a reagent for detecting the presence of human antibodies bound to said support.

* * * * *